(12) United States Patent
Pinto

(10) Patent No.: US 8,084,276 B2
(45) Date of Patent: *Dec. 27, 2011

(54) METHOD FOR IDENTIFYING A SUBJECT AT RISK OF DEVELOPING HEART FAILURE BY DETERMINING THE LEVEL OF GALECTIN-3 OR THROMBOSPONDIN-2

(75) Inventor: Yigal M. Pinto, Amstelveen (NL)

(73) Assignee: Universiteit Maastricht, Maastricht (NL)

( * ) Notice: Subject to any disclaimer, the term of this patent is extended or adjusted under 35 U.S.C. 154(b) by 0 days.

This patent is subject to a terminal disclaimer.

(21) Appl. No.: 12/914,329

(22) Filed: Oct. 28, 2010

(65) Prior Publication Data

US 2011/0104722 A1 May 5, 2011

Related U.S. Application Data

(63) Continuation of application No. 10/575,745, filed as application No. PCT/EP2004/010879 on Sep. 27, 2004, now Pat. No. 7,888,137.

(30) Foreign Application Priority Data

Oct. 9, 2003 (EP) ..................................... 03078161

(51) Int. Cl.
*G01N 33/53* (2006.01)
(52) U.S. Cl. ...................................... 436/811; 435/7.92
(58) Field of Classification Search .......................... None
See application file for complete search history.

(56) References Cited

U.S. PATENT DOCUMENTS

| | | | |
|---|---|---|---|
| 4,632,901 A | 12/1986 | Valkirs et al. | |
| 4,704,692 A | 11/1987 | Ladner | |
| 4,946,778 A | 8/1990 | Ladner et al. | |
| 5,091,513 A | 2/1992 | Huston et al. | |
| 5,132,405 A | 7/1992 | Huston et al. | |
| 6,319,676 B1 | 11/2001 | Nazareth et al. | |
| 6,485,982 B1 | 11/2002 | Charlton | |
| 6,534,322 B1 | 3/2003 | Sabbadini | |
| 6,889,083 B2 | 5/2005 | Kleckner et al. | |
| 2002/0076738 A1 | 6/2002 | Woo | |
| 2003/0032030 A1 | 2/2003 | Prolla et al. | |
| 2003/0166017 A1 | 9/2003 | McCarthy | |
| 2004/0110221 A1 | 6/2004 | Twine et al. | |
| 2005/0084915 A1 | 4/2005 | Woo | |
| 2005/0106100 A1 | 5/2005 | Harris et al. | |
| 2006/0019235 A1 | 1/2006 | Soen et al. | |
| 2006/0019890 A1 | 1/2006 | Kapoun et al. | |
| 2006/0141493 A1 | 6/2006 | West et al. | |
| 2006/0166276 A1 | 7/2006 | Doyle et al. | |
| 2006/0246496 A1 | 11/2006 | Ahmed et al. | |
| 2006/0257946 A1 | 11/2006 | Ding et al. | |
| 2007/0082332 A1 | 4/2007 | Mendrick et al. | |
| 2007/0092886 A1 | 4/2007 | Tabibiazar et al. | |
| 2007/0105105 A1 | 5/2007 | Clelland et al. | |
| 2007/0274959 A1 | 11/2007 | Zeiher et al. | |
| 2010/0014954 A1 | 1/2010 | Henderson | |
| 2010/0143954 A1 | 6/2010 | Muntendam | |
| 2011/0071583 A1 | 3/2011 | Muntendam | |

FOREIGN PATENT DOCUMENTS

| | | |
|---|---|---|
| WO | WO-0157274 A2 | 8/2001 |
| WO | WO-0177389 A2 | 10/2001 |
| WO | WO-03031650 A2 | 4/2003 |
| WO | WO-03071279 A1 | 8/2003 |
| WO | WO-2004038376 A2 | 5/2004 |
| WO | WO-2004048933 A2 | 6/2004 |
| WO | WO-2004063334 A2 | 7/2004 |
| WO | WO-2004111654 A2 | 12/2004 |
| WO | WO-2005023314 A1 | 3/2005 |
| WO | WO-2005070446 A1 | 8/2005 |
| WO | WO-2006026074 A2 | 3/2006 |
| WO | WO-2006083986 A2 | 8/2006 |

OTHER PUBLICATIONS

Almkvist et al. (2004) "Galectins as inflammatory mediators," *Glyconconj J.* 19:575-581.
Cooper (2002) "Galectinomics: Finding themes in complexity," *Biochim Biophys Acta.* 1572:209-231.
Hsu et al. (1999) "Galectin-3 expression is induced in cirrhotic liver and hepatocellular carcinoma," *Int J Cancer* 81:519-26.
Kasper et al. (1996) "Immunocytochemical evidence for a modulation of galectin-3 (mac2), a carbohydrate binding protein, in pulmonary fibrosis," *J Pathol.* 179:309-316.
Ochieng et al. (2004) "Extracellular functions of galectin-3" *Glycoconj J.* 19:527-535.
Sano et al.(2003) "Critical role of galectin-3 in phagocytosis by macrophages," *J Clin Invest.* 112:389-397.
Ahmed et al. (2007) "Advanced Glycation Endproducts: What is their relevance to diabetic complications?" *Diabetes, Obesity and Metabolism* 9(3): 233-245.
Andre et al. (2001) "Wedgelike Glycodendrimers as Inhibitors of Binding of Mammalian Galectins to Glycoproteins, Lactose Maxiclusters, and Cell Surface Glycoconjugates," *Chembiochem* 2: 822-830.
Aragno et al. (2005) "Up-regulation of advanced glycated products receptors in the brain of diabetic rats is prevented by antioxidant treatment," *Endocrinology* 146(12): 5561-5567.
Aragno et al. (2006) "Oxidative Stress-Dependent Impairment of Cardiac-Specific Transcription Factors in Experimental Diabetes," *Endocrinology* 147(12): 5967-5974.
Bandman et al. (2002) "Complexity of Inflammatory Responses in Endothelial Cells and Vascular Smooth Muscle Cells Determined by Microarray Analysis," *Ann. N.Y. Acad. Sci.* 975: 77-90.
Bender MedSystems product information and manual for enzyme-linked immunosorbent assay for quantitative detection of human Galectin-3, BMS279/2, dated Aug. 24, 2006, 32 pages.
Bohlender et al. (2005) "Advanced glycation end products and the kidney," American Journal of Physiology: Renal Physiology 289: F645-F659.
Bolli (2002) "Clinical strategies for controlling peaks and valleys: type 1 diabetes " *IJCP* 10 pages.

(Continued)

Primary Examiner — Melanie J Yu
Assistant Examiner — Gary W Counts
(74) Attorney, Agent, or Firm — Goodwin Procter LLP

(57) ABSTRACT

Described herein are methods for identifying a subject at risk of progression of heart failure. In some embodiments, the level of galectin-3 in a biological sample from a human subject may be measured and compared to a standard level indicative of risk of progression of heart failure, wherein an elevated level of galectin-3 in the sample indicates a risk of progression of heart failure.

6 Claims, 13 Drawing Sheets

OTHER PUBLICATIONS

Figure 1:
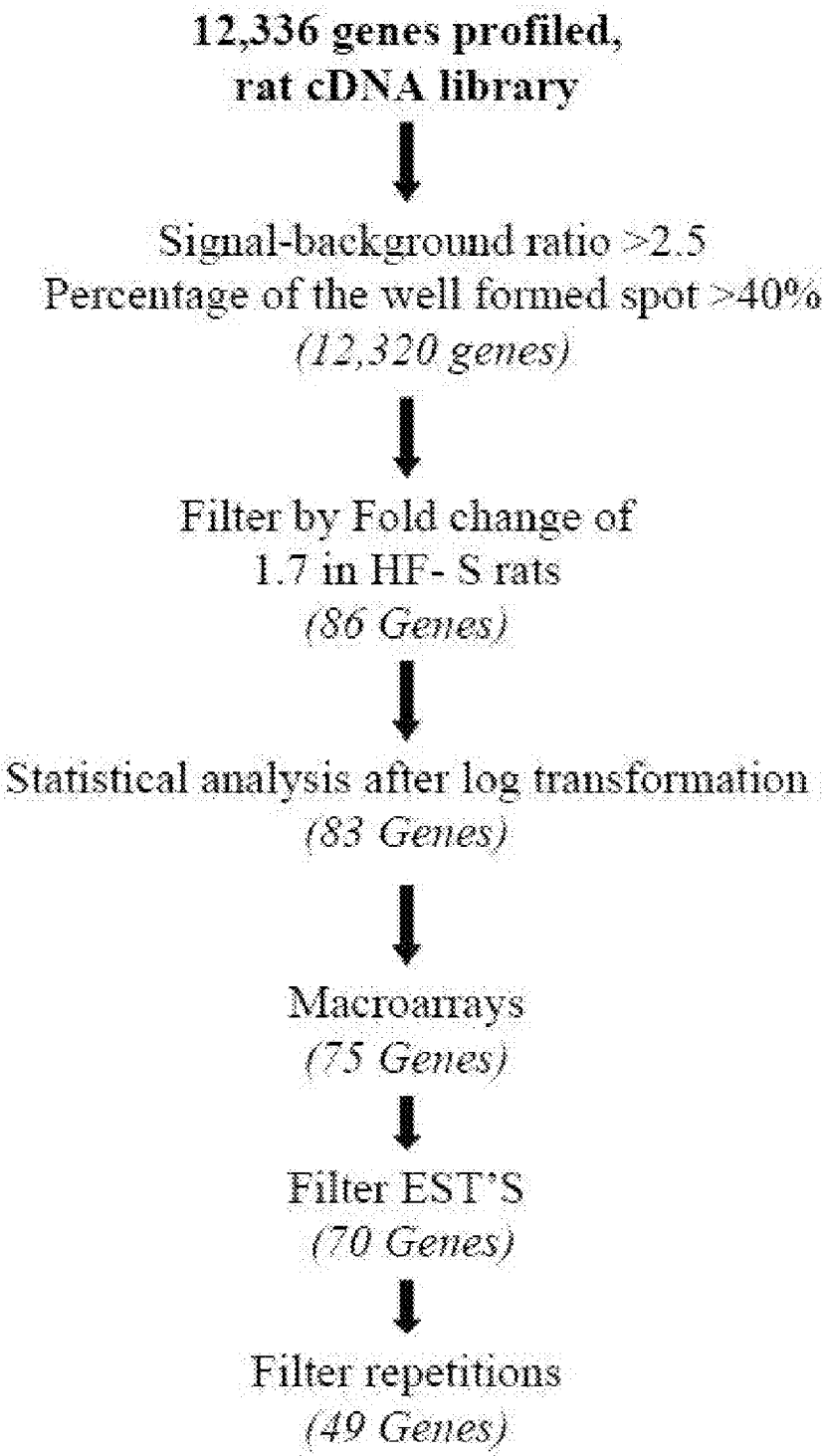

Boluyt et al. (1995) "The ageing spontaneously hypertensive rat as a model of the transition from stable compensated hypertrophy to heart failure," *European Heart Journal* 19-30.

Boluyt et al. (1995) "The lonely failing heart: a case for ECM genes," *Cardiovascular Research* 835-340.

Boluyt et al. (2000) "Matrix gen expression and decompensated heart failure: The aged SHR model," *Cardiovascular Research* 239-249.

Broers et al. (1999) "Dynamics of the nuclear lamina as monitored by GFP-tagged A-type lamins," *Journal of Cell Science* 3463-3475.

Brooks et al. (1997) "Captopril Modifies Gene Expression in Hypertrophied and Failing Hearts of Aged Spontaneously Hypertensive Rats," *Hypertension* 1362-1368.

Cameselle-Teijeiro et al. (2005) "Cystic tumor of the atrioventricular node of the heart appears to be the heart equivalent of the solid cell nests (ultimobranchial rests) of the thyroid," *American Journal of Clinical Pathology* 123(3): 369-375.

Cheng et al. (2007) "Differential neuroprotective effects of a minocycline-based drug cocktail in transient and permanent focal cerebral ischemia," *Experimental Neurology* 204(1): 433-442.

Cherayil et al. (1990) "Molecular cloning of a human macrophage lectin specific for galactose," *Proc. Natl. Acad. Sci. USA* 7324-7328.

Cleutjens et al. (1995) "Collagen Remodeling after Myocardial Infarction in the Rat Heart," *American Journal of Pathology* 325-338.

Cleutjens et al. (1999) "Thrombospondin 2 Deficiency in Mice Results in Cardiac Rupture Early after Myocardial Infarction," *Circulation* (abstract).

Gabius (1990) "Influence of Type of Linkage and Spacer on the Interaction of beta-Galactoside-Binding Proteins with Immobilized Affinity Ligands," *Analytical Biochemistry* 91-94.

Giordanengo et al. (2001) "Anti-galectin-1 autoantibodies in human Trypansosoma cruzi infection: differential expression of this β-galactosie-binding protein in cardiac Chagas' disease," *Clinc. Exp. Immunology* 266-273.

Hein et al. (2003) "Progression From Compensated Hypertrophy to Failure in the Pressure-Overloaded Human Heart: Structural Deterioration and Compensatory Mechanism," *Journal of the American Heart Association* 984-991.

International Preliminary Report for International Application No. PCT/EP2004/10879, mailed Sep. 20, 2005.

Iurisci et al. (2000) "Concentrations of Galectin-3 in the Sera of Normal Controls and Cancer Patients," *Clinical Cancer Research* 6:1389-1393.

Kankova et al. (2005) "Haplotype Analysis of the RAGE gene: Identification of a Haplotype Marker for Diabetic Nephropathy in Type 2 Diabetes Mellitus," *Nephrology, Dialysis, Transplantation* 20(6): 1093-1102.

Karlsen et al.(2006) "Immune-mediated beta-cell destruction in vitro and in vivo—A pivotal role for galectin-3," *Biochemical and Biophysical Research Communications* 344(1): 406-415.

Kostin et al. (2003) "Mycocytes Die by Multiple Mechanisms in Failing Human Hearts," *Circulation Research* 1-10.

Liehn et al. (2005) "CCR5-but not CCR1-deficiency protects against neointima formation in apolipoprotein E-deficient mice," *European Heart Journal* 26(Suppl 1): 239.

Liu et al. (2009) "Angiotensin-converting Enzyme is a Modifier of Hypertensive End Organ Damage," *Journal of Biological Chemistry* 284(23): 15564-15572.

Lok et al. (2007) "Galectin-3, a novel marker of macrophage activity, predicts outcome in patients with stable chronic heart failure," *Journal of the American College of Cardiology* 49(9) Suppl. A: 98A.

Lorell et al. (2000) "Left Ventricular Hypertrophy: Pathogenesis, Detection, and Prognosis," *Circulation* 470-479.

Luft et al. (1999) "Hypertension-Induced End-Organ Damage: A New Transgenic Approach to an Old Problem," *Hypertension* 33: 212-218.

Mathews et al. (1995) "Evidence for IgG Autoantibodies to Galectin-3, a β-Galactoside-Binding Lectin (Mac-2, ε Binding Progtein, or carboyhdrate Binding Protein 35) in Human Serum," *Journal of Clinical Immunology* 329-336.

McCowan et al. (2009) "Hypertensive Emergencies," *Emedicine* 1-23.

Mensah-Brown et al. (2006) "Functional Capacity of Macrophages Determines the Induction of Type 1 Diabetes," *Annals of the New York Academy of Sciences* 1084: 49-57.

Mita et al. (2007) "Swings in blood glucose levels accelerate atherogenesis in apolipoprotein E-deficient mice," *Biochemical and Biophysical Research Communications* 358(3): 679-685.

Moore et al. (2005) "Using Peripheral Blood Mononuclear Cells to Determine a Gene Expression Profile of Acute Ischemic Stroke: A Pilot Investigation," *Circulation* 111(2): 212-221.

Panidis (1984) "Development and Regression of Left Ventricular Hypertrophy," *Journal by the American College of Caridiology* 1309-30.

Papaspyridonos et al. (2006) "A Potential Role for Galectin-3 in Atherosclerotic Plaque Progression through Monocyte Chemoattraction and Macrophage Activation" *Atherosclerosis* 186(2): S3.

PCT Search Report and Written Opinion for International Application No. PCT/EP2004/10879, mailed Nov. 25, 2004, 14 pages.

Pieters (2006) "Inhibition and Detection of Galectins," *Chem Bio Chem* 7:721-728.

Pokharel et al. (2002) "N-Acetyl-Ser-Asp-Lys-Pro Inhibits Phosphorylation of Smad2 in Cardiac Fibroblasts," *Hypertension* 155-161.

Pugliese et al. (2006) "Increased Glomerular Cell (Podocyte) Apoptosis in Rats with Streptozotocin-induced Diabetes Mellitus: Relation to Increased p53 Expression," *Diabetologia* 49(Suppl 1): 651-652.

Reifenberg et al. (2007) "Interferon-gamma Induces Chronic Active Myocarditis and Cardiomyopathy in Transgenic Mice," *American Journal of Pathology* 171(2): 463-472.

Schroen et al. (2003) "Genomic analysis identifies Thrombospondin-2 as a molecular predictor of heart failure," *Circulation* 108(17 Suppl.):IV-260.

Schroen et al. (2007) "Lysosomal Integral Membrane Protein 2 is a Novel Component of the Cardiac Intercalated Disc and Vital for Load-induced Cardiac Myocyte Hypertrophy," *Journal of Experimental Medicine* 204(5): 1227-1235.

Scott-Burden et al. (1998) "Modulation of Extracellualr Matrix by Angiotensin II: Stimulated Glycoconjugate Synthesis and Growth in Vascular Smooth Muscle Cells," *Journal of Cardiovascular Pharmacology* 16(Suppl. 4):S36-S41.

Sharma et al. (2003) "Galectin-3 is a novel macrophage derived mediator of cardiac fibrosis and specifically marks failing hearts," *Circulation* 108(17 Suppl.):IV-260.

Sharma et al. (2004) "Galectin-3 Marks Activated Macrophages in Failure-Prone Hypertrophied Hearts and Contributes to Cardiac Dysfunction," *Circulation* 110:3121-3128.

Sharma et al. (2005) "Early growth regulator-1 mediates galectin-3 induced cardiac fibrosis," *Hypertension* 46(4): 819-820.

Sharma et al. (2005) "Mice lacking galectin-3 exhibit preserved cardiac function and decreased fibrosis following angiotensin II infusion," *Circulation* 112(17) Suppl S: II-64.

Sharma et al.(2007) "Novel Anti-inflammatory Mechanisms of Ac-SDKP in High Blood Pressure-induced Target Organ Damage," *Circulation* 114(18) Suppl S: 240.

Shirakata et al. (2001) Inverse regulation of the angiogenesis factor VEGF and the angiogenesis inhibitors Thrombospondin-1 and TSP-2 in human epidermal keratinocytes, *Journal of Investigative Dermatology* 117(2):391.

Stitt et al. (2005) "Impaired Retinal Angiogenesis in Diabetes: Role of Advanced Glycation End Products and Galectin-3," *Diabetes* 54(3): 785-794.

Tan et al. (2002) "The gene expression fingerprint of human heart failure," *PNAS* 11387-11392.

Tan et al. (2007) "AGE, RAGE and ROS in Diabetic Neuropathy," *Seminars in Nephrology* 27(2): 130-143.

Tang et al. (2007) "National Academy of Clinical Biochemistry Laboratory Medicine Practice Guidelines; Clinical Utilization of Cardiac Biomarker Testing in Heart Failure," *Circulation* 116(5): e99-e109.

Topol et al. (2001) "Single Nucleotide Polymorphisms in Multiple Novel Thromboxpondin Genes May Be Associated With Familial Premature Myocardial Infarction " *Circulation* 2641-2644.

van Kimmenade et al. (2005) "Galectin-3 predicts 60 days mortality in heart failure: A step towards multimarker strategy in heart failure. Results from the ProBNP investigation of dyspnea in the emergency department (PRIDE) study," *Circulation* 112(17) Suppl S: II-669.

van Kimmenade et al. (2006) "Utility of Amino-Terminal Pro-Brain Natriuretic Peptide, Galectin-3, and Apelin for the Evaluation of Patients With Acute Heart Failure," *Journal of the American College of Cardiology* 48(6):1217-1224.

Vasan et al. (2003) "Inflammatory Markers and Risk of Heart Failure in Elderly Subjects Without Prior Myocardial Infarction: The Framingham Heart Study," *Circulation* 1486-1491.

Wada et al. (2001) "Galectins, Galactoside-Binding Mammalian Lectins: Clinical Application of Multi-Functional Proteins," *Acta Med. Okayama* 55(1):11-17.

Walton et al. (2003) "Thrombospondin-2 and lymphotoxin-alpha gene variations predict coronary heart disease in a large prospective study,"*Circulation* 108(17 Suppl.):IV-260.

Zhang et al. (2003) "The role of the Brb2-p38 MAPK signaling pathway in cardiac hypertrophy and fibrosis," *J. Clinical Investigation* 833-841.

Barboni et al. (2000) "Molecular modeling and mutagenesis studies of the N-terminal domains of galectin-3: evidence for participation with the C-terminal carbohydrate recognition domain in oligosaccharide binding," *Glycobiology* 10:1201-8.

Barondes et al. (1994) "Galectins: A family of Animal β-Galactoside-Binding Lectins," *Cell* 76:597-8.

Braunwald (2008) "Biomarkers in heart failure," *N. Engl. J. Med.* 20:2148-59.

Beshai et al. (2007) "Cardiac-Resynchronization Therapy in Heart Failure with Narrow QRS Complexes," *N. Engl. J. Med.* 357:2461-2471.

BGM Galectin-3 assay; Product Insert (US); BG Medicine, Inc., Mar. 9, 2011.

Christenson et al. (2010) "Multi-center determination of galectin-3 assay performance characteristics: anatomy of a novel assay for use in heart failure," *Clin. Biochem.* 43:683-90.

Clackson et al. (1991) "Making antibody fragments using phage display libraries," *Nature* 352:624-628.

Cleland et al. (2005) "The Effect of Cardiac Resynchronization on Morbidity and Mortality in Heart Failure," *New Engl. J. Med.* 352:1539-49.

Cohn et al. (2000) "Cardiac remodeling—concepts and clinical implications: a consensus paper from an international forum on cardiac remodeling," *J. Am. Coll. Cardiol.* 35:569-82.

Cosson (2004) "Usefulness of B-type natriuretic pepetide (BNP) as a screen for left ventricular abnormalities in diabetes mellitus," *Diabetes Metab.* 30, 381-6.

Czekalski (2007) "BNP concentrations in diabetics with dyspnea," printed on Sep. 14, 2007, 4 pages.

de Boer et al. (2010) "Clinical and prognostic value of galectin-3: a novel fibrosis-associated biomarker. Relation with clinical and biochemical correlates of heart failure," *J. Am. Coll. Cardiol.* 55:A26. (Presented at the American College of Cardiology Annual Scientific Session, Mar. 14, 2010, Atlanta, GA).

de Boer et al. (2009) "Galectin-3: a novel mediator of heart failure development and progression," *Eur. Heart J.* 11:811-817.

de Boer et al. (2010) "Galectin-3 in cardiac remodeling and heart failure," *Curr. Heart Fail. Rep.* 7:1-8.

de Boer et al. (2011) "Predictive value of plasma galectin-3 levels in heart failure with reduced and preserved ejection fraction,"*Ann. Med.* 43(1):60-68.

de Couto et al. (2010) "Early detection of myocardial dysfunction and heart failure," *Nat. Rev. Cardiol.* 7(6):334-344.

deFilippi et al. (2009) "Clinical validation of a novel assay for galectin-3 for risk assessment in acutely destabilized heart failure,"*J. Card. Fail.* 5:S9. (Presented at the Heart Failure Society of America Annual Scientific Meeting, 2009, Boston, MA).

deFilippi et al. (2010) "Galectin-3 in heart failure—linking fibrosis, remodeling, and progression," *US Cardiology* 7:67-70.

Dumic et al. (2006) "Galectin-3: an open-ended story." *Biochim. Biophys. Acta* 1760:616-635.

Duray et al. (2008) "Upgrading to biventricular pacing/defibrillation systems in right ventricular paced congestive heart failure patients: prospective assessment of procedural parameters and response rate," *Europace* 10:48-52.

Epshteyn (2003) "Utility of B-type natriuretic peptide (BNP) as a screen for left ventricular dysfunction in patients with diabetes," *Diabetes Care* 26(7):2081-2087.

Felker et al. (2010) "Prognostic value of galectin-3 in chronic heart failure: results from the HF-ACTION study." (Presented at the European Society of Cardiology Congress, 2010, Stockholm, Sweden).

Francia et al. (2007) "Cardiac resynchronization therapy increases plasma levels of the endogenous inotrope apelin," *Eur. J. Heart Fail.* 9(3):306-309.

Fruhwald et al. (2007) "Early and sustained effects of cardiac resynchronization therapy on N-terminal pro-B-type natriuretic peptide in patients with moderate to severe heart failure and cardiac dyssynchrony " *Eur. Heart J.* 28:1592-1597.

Gabius (2006) "Cell Surface Glycans: The Why and How of Their Functionality as Biochemical Signals in Lectin-Mediated Information Transfer," *Crit. Rev. Immunol.* 26:43-79.

Grandin et al. (2011) "Galectin-3 and the development of heart failure after acute coronary syndrome: A pilot experience from PROVE IT-TIMI 22," *J. Am. Coll. Cardiol.* 57:69.

Hagberg (1998) "From magnetic resonance spectroscopy to classification of tumors. A review of pattern recognition methods," *NMR Biomed.* 11:148-156.

Hawkins et al. (2006) "Selecting patients for cardiac resynchronization therapy: electrical or mechanical dyssynchrony?," *Eur. Heart J.* 27:1270-1281.

Henderson et al. (2008) "Galectin-3 expression and secretion links macrophages to the promotion of renal fibrosis," *Am. J. Pathol.* 172:288-298.

Henderson et al. (2006) "Galectin-3 regulates myofibroblast activation and hepatic fibrosis,"*Proc. Natl. Acad. Sci. USA* 103:5060-5065.

Henderson (2009) "The regulation of inflammation by galectin-3," *Immunol. Rev.* 230:160-71.

International Search Report and Written Opinion for International Application No. PCT/US2010/046689 dated May 18, 2011, 10 pages.

Jeevantham et al. (2009) "Cardiac resynchronization therapy in heart failure patients: An update," *Cardiol. J.* 16(3):197-209.

Kim et al. (2007) "Expression and immunohistochemical localization of galectin-3 in various mouse tissues," *Cell Biol. Int.* 31:655-662.

Kolatsi-Joannou et al. (2011) "Modified citrus pectin reduces galectin-3 expression and disease severity in experimental acute kidney injury," *PLoS One* 6(4):e18683.

Kuwabara et al. (1996) "Galectin-3 Promotes Adhesion of Human Neutrophils to Laminin," *J. Immunol.* 156(10):3939-3944.

Lainscak et al. (2010) "Clinical trials update from the Heart Failure Society of America Meeting 2009: FAST, IMPROVE-HF, COACH galectin-3 substudy, HF-ACTION nuclear substudy, DAD-HF, and MARVEL-1," *Eur. J. Heart Fail.* 12(2):193-196.

Lambert et al. (2008) "Macrophage roles following myocardial infarction," *Int. J. Cardiol.* 130:147-158.

Leclercq et al. (2002) "Retiming the failing heart: principles and current clinical status of cardiac resynchronization " *J. American Coll. of Card.* 39:194-201.

Lin et al. (2009) "The relationship between serum galectin-3 and serum markers of cardiac extracellular matrix turnover in heart failure patients," *Clin. Chim. Acta* 409:96-99.

Liu et al. (2009) "N-acetyl-seryl-aspartyl-lysyl-proline prevents cardiac remodeling and dysfunction induced by galectin-3, a mammalian adhesion/growth-regulatory lectin," *Am. J. Physiol. Heart Circ. Physiol.* 296:H404-H412.

Lok et al. (2007) "Relationship between galectin-3 and NT pro-BNP and outcome in patients with chronic congestive heart failure," *Eur. Heart J.* 28:141, Abstract 1035, http://cic.escardio.org/abstractdetails.aspx?id-50976&eevtid-19, 1 page.

Lok et al. (2010) "Plasma galectin-3 levels predict left ventricular remodeling determined by sequential echocardiography: results from the Deventer-Alkmaar heart failure study," *J. Am. Coll. Cardiol.*

55:A17. (Presented at the American College of Cardiology Annual Scientific Session, Mar. 16, 2010, Atlanta, GA).

Lok et al. (2010) "Prognostic value of galectin-3, a novel marker of fibrosis, in patients with chronic heart failure: data from the DEAL-HF study," *Clin. Res. Cardiol.* 99:323-328.

Lukyanov et al. (2005) "Galectin-3 interacts with membrane lipids and penetrates the lipid bilayer," *Biochem. Biophys. Res. Commun.* 338:1031-1036.

Menon et al. (1999) "Determinants in the N-terminal domains of galectin-3 for secretion by a novel pathway circumventing the endoplasmic reticulum-Golgi complex." *Eur. J. Biochem.* 264:569-576.

Milting et al. (2008) "Plasma biomarkers of myocardial fibrosis and remodeling in terminal heart failure patients supported by mechanical circulatory support devices," *J. Heart Lung Transplant.* 27:589-596.

Muntendam et al. (2009) "Reference interval for plasma galectin-3 in healthy subjects age 55 years and older," *Clin. Chem.* 55:B72. (Presented at the American Association for Clinical Chemistry Annual Meeting, Jul. 21, 2009, Chicago, IL).

Nesto (2007) "CHF in Diabetes: Implications for the Use of TZDs (Slides with Transcript)," http://cme.medscape.com/viewarticle560872_print, 17 pages.

Nesto et al. (2003) "Thiazolidinedione use, fluid retention, and congestive heart failure: a consensus statement from the American Heart Association and American Diabetes Association," *Circulation* 108(23):2941-2948.

Nishi et al. (2007) "Role of galectin-3 in human pulmonary fibrosis," *Allergol. Int.* 56:57-65.

Opie et al. (2006) "Controversies in ventricular remodelling," *Lancet* 367:356-367.

Ogawa et al. (2003) "Plasma BNP levels in the treatment of type 2 diabetes with pioglitazone," *J. Clin. Endocrinol. Metabol.* 88(8):3993-3996.

"Panel Discussion (Slides with Transcript)," published Aug. 8, 2007, http://cme.medscape.com/viewarticle/560873, 6 pages.

Plutzky (2007) "What Do We Know About Surrogate Markers and Disease Outcomes? (Slides with Transcript)," http://cme.medscape.com/viewarticle/560871_print, 13 pages.

Psarras et al. (2011) "Regulation of adverse remodelling by osteopontin in a genetic heart failure model," *Eur. Heart J.* Epub Jul. 20, 2011.

Rossignol et al. (2010) Galectin-3 and PIIINP are associated with cardiovascular outcomes in patients with heart failure, left ventricular dysfunction and dysynchrony. Insights from the CARE-HF study. (Presented at the European Society of Cardiology Congress, 2010, Stockholm, Sweden).

Rovner et al. (2007) "Relation of Left Ventricular Lead Placement in Cardiac Resynchronization Therapy to Left Ventricular Reverse Remodeling and to Diastolic Dyssynchrony," *Am. J. Cardiol.* 99:239-241.

Sano et al. (2000) "Human Galectin-3 is a novel chemoattractant for monocytes and macrophages," *J. Immunol.* 165(4):2156-2164.

Sasaki et al. (1999) "Galectin-3 modulates rat mesangial cell proliferation and matrix synthesis during experimental glomerulonephritis induced by anti-Thy1.1 antibodies," *J. Panthol.* 187:481-489.

Sathisha et al. (2007) "Inhibition of galectin-3 mediated cellular interactions by pectic polysaccharides from dietary sources," *Glycoconj. J.* 24:497-507.

Sato et al. (2008) "Galectins as danger signals in host-pathogen and host-tumor interactions: new members of the growing group of alarmins"? in *Galectins*, John Wiley & Sons; Eds: Klyosov AA, Witczak, ZJ, Platt D. 2008; DOI:10.1002/9780470378076.ch7.

Seetharaman et al. (1998) "X-ray crystal structure of the human galectin-3 carbohydrate recognition domain at 2.1-A resolution," *J. Biol. Chem.* 273:13047-13052.

Shah et al. (2010) "Galectin-3, cardiac structure and function, and long-term mortality in patients with acutely decompensated heart failure," *Eur. J. Heart Fail.* DOI:10.1093/eurjhf/hfq091.

Shah et al. (2010) "Galectin-3, cardiac structure and function, and long-term mortality in patients with acute heart failure," *J. Am. Coll. Cardiol.* 55:A34. (Presented at the American College of Cardiology Annual Scientific Session, Mar. 15, 2010, Atlanta, GA).

Sharma et al. (2008) "Novel anti-inflammatory mechanisms of N-acetyl-ser-asp-lys-pro in hypertension-induced target organ damage," *Am. J. Physiol. Heart Circ. Physiol.* 294:H1226-1232.

Sherwi et al. (2010) "Does the severity of LV dysfunction or the extent of myocardial scar explain elevations in plasma galectin-3 in patients with heart failure?" *Eur. J. Heart Fail. Suppl.* 9:S18.

Smith et al. (2009) "Analytical performance of an optimized ELISA for galectin-3," *Clin. Chem.* 55:B69.

Son (2007) "Cardiomyocyte expression of PPARγ leads to cardiac dysfunction in mice," *J. Clin. Invest.* 117:2791-2801.

Stellbrink (2007) "Its the metabolism, stupid! Why electrophysiologists should be interested in biomarkers of heart failure," *Eur. Heart J.* 28:1541-1542.

Tang et al. (2011) "Usefulness of plasma galectin-3 levels in systolic heart failure to predict renal insufficiency and survival," *Am. J. Cardiol.* 108(3):385-390.

Ueland et al. (2011) "Galectin-3 in heart failure: high levels are associated with all-cause mortality," *Int. J. Cardiol.* 150(3):361-364.

van Veldhuisen et al. (2009) "Clinical and prognostic value of galectin-3, a novel fibrosis-associated biomarker, in patients with chronic heart failure," *J. Card. Fail.* 15:814.

Wu (2004) "The effect of diabetes on B-type natriuretic peptide concentrations in patients With acute dyspnea," *Diabetes Care* 27(10):2398-2404.

Yanavitski et al. (2011) "Novel biomarkers in acute heart failure," *Curr. Heart Fail. Rep.* 8(3):206-211.

Yang et al. (2008) "Galectins: Structure, function and therapeutic potential," *Expert Rev. Mol. Med.* 13:e17-e39.

Zile et al. (2010) "Plasma galectin-3 levels in patients with structural and clinical manifestations of hypertensive heart disease: relationship to determinants of matrix composition." (Presented at the American Heart Association Scientific Sessions, 2010, Chicago, IL).

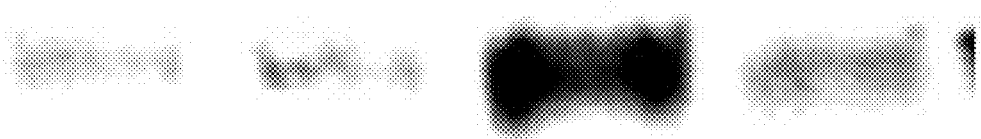
SD   HF-R   HF-S   ARB
FIG. 9A1
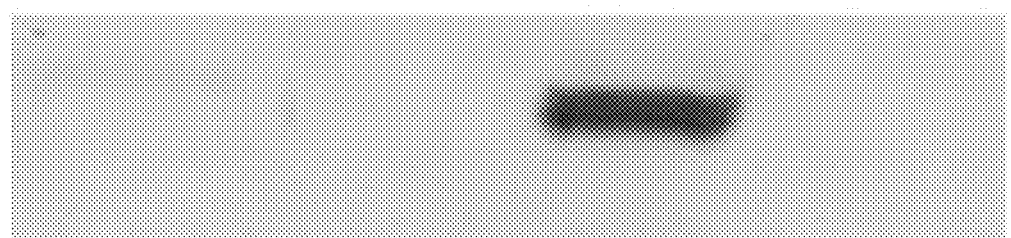
SD   HF-R   HF-S   ARB
FIG. 9B1

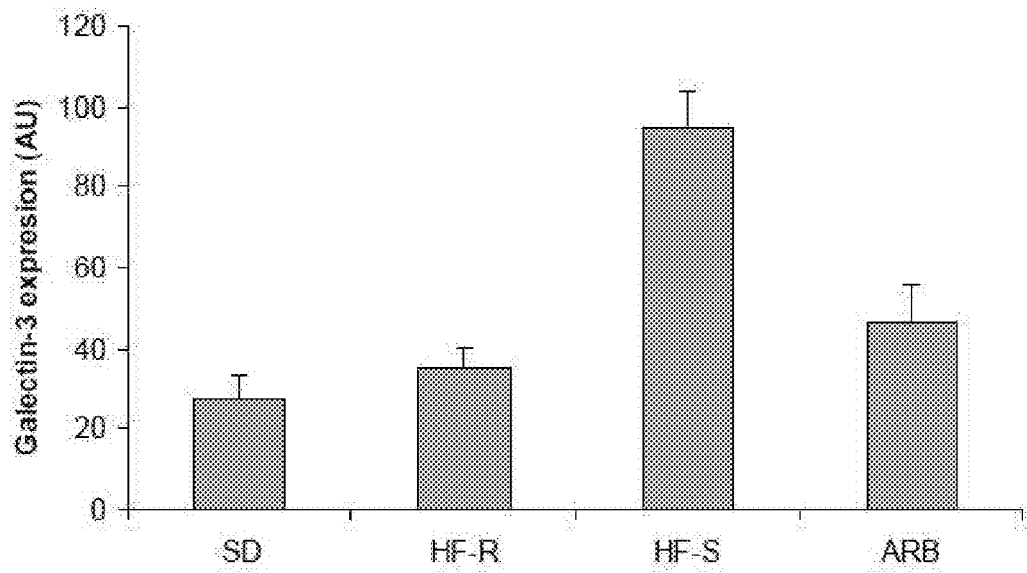
FIG. 9A2
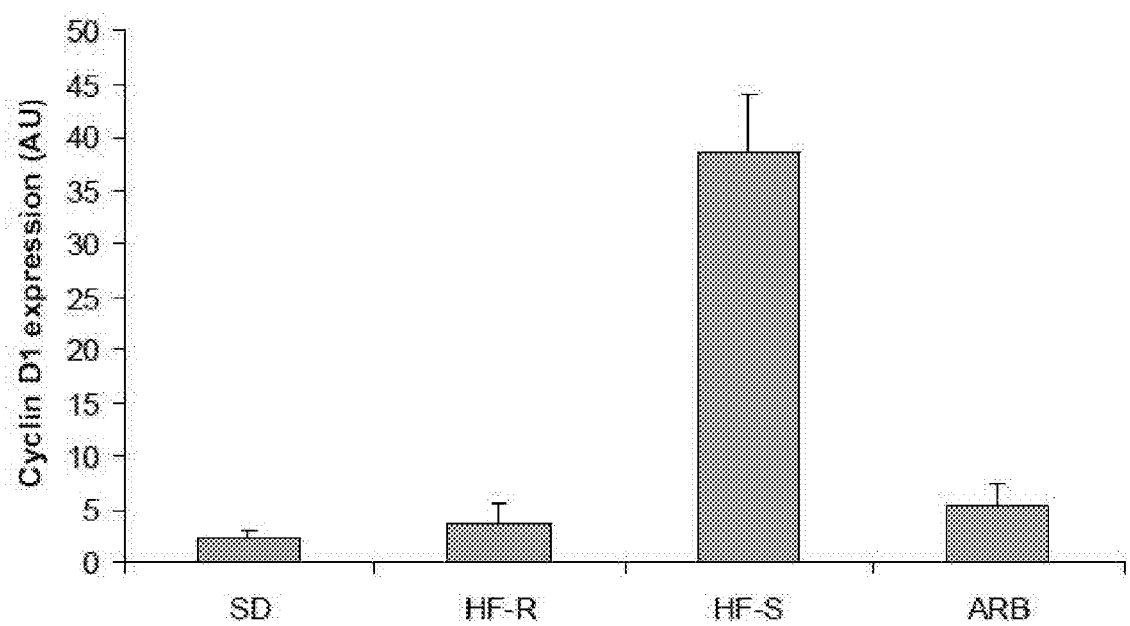
FIG. 9B2

METHOD FOR IDENTIFYING A SUBJECT AT RISK OF DEVELOPING HEART FAILURE BY DETERMINING THE LEVEL OF GALECTIN-3 OR THROMBOSPONDIN-2

REFERENCE TO RELATED APPLICATIONS

This application is a continuation application of U.S. application Ser. No. 10/575,745, now U.S. Pat. No. 7,888,137, filed Apr. 9, 2007, which is a national stage of International (PCT) Patent Application No. PCT/EP2004/010879, filed Sep. 27, 2004, and published under PCT Article 21(2) in English, which claims the benefit of and priority to European Patent Application No. 03078161.1 filed Oct. 9, 2003. The entire disclosure of U.S. application Ser. No. 10/575,745 is incorporated by reference herein.

The present invention relates to a method for identifying a subject at risk of developing hypertensive end organ damage, such as congestive heart failure.

Congestive heart failure (HF) is a common but severe and complex clinical syndrome, especially among elderly people, characterized by a diminished cardiac contractile function and decreased exercise tolerance, resulting in a gradual detoriation of the patient often leading to cardiovascular mortality. Thus, a large number of patients die within one to five years after diagnosis. However, although an important number of patients progress to develop life threatening complications, other may remain stable for prolonged periods.

As early identification of patients at risk for developing hypertensive end organ damage, such as heart failure, may prevent rapid progression, it would be preferable to be able to identify those patients in which heart failure is likely to occur before it actually does so. In addition, it would be preferable to be able to identify those patients suffering from heart failure who are at risk for developing severe complications.

Current methods can reliably exclude heart failure, but cannot reliably prove the existence of heart failure, nor can they predict the outcome of established heart failure, or require expensive equipment and specifically trained personnel to do so.

A need therefore exists for a simple and reliable method for predicting the likelihood of onset of heart failure and for predicting the outcome of already established heart failure.

The object of the present invention is to provide a method by which patients can be identified who are at particular risk of developing hypertensive end organ damage, such as heart failure, or who are at particular risk to develop complications of heart failure. After identification, these patients may for example be treated before heart failure or its complications occur, which would be of great clinical importance.

This is achieved by the invention by providing a method for identifying a subject at risk of developing hypertensive end organ damage, comprising the steps of:

(a) obtaining a biological sample of said subject;
(b) determining the level of at least one non-myocytical marker in said sample;
(c) comparing the level of said marker to a standard level; and
(d) determining whether the level of the marker is indicative of a risk for developing hypertensive end organ damage.

In the research that led to the present invention specific markers were identified that can be used to predict which hypertrophied hearts are prone to failure.

It is generally known that hypertension causes cardiac hypertrophy, which is one of the most important risk factors for heart failure. However, not all hypertrophied hearts will ultimately fail. These observations suggest that additional mechanisms, besides those that cause hypertrophy, are recruited during the progression from compensated cardiac hypertrophy to failure. Although recent studies have reported many molecular and cellular changes underlying cardiac hypertrophy (Lorell B H et al., Circulation 102: 470-479, 2000; Panidis et al., J Am Coll Cardiol. 3: 1309-1320, 1984), the additional factors that contribute to heart failure have remained unclear until now.

Boluyt and co-workers have for example documented the upregulation of genes encoding extracellular matrix (ECM) components in spontaneously hypertensive rats (SHR) with heart failure (Boluyt et al., Cardiovasc Res. 46: 239-249, 2000; Hypertension 30: 1362-1368, 1997; Cardiovasc Res. 30: 836-840, 1995; Eur Heart J. 16 suppl. N: 19-30, 1995). However, it is not clear whether the overexpression of these genes preceded the overt clinical syndrome of heart failure or whether their overexpression was rather a consequence of an established process of active failure.

Several other unbiased approaches have also been employed to identify mechanisms specific for heart failure (Korstin S et al., Circ Res. 92: 715-724, 2003; Hein S et al., Circulation 107: 984-991, 2003). In addition, recent studies have suggested that immune mechanisms are specifically activated in failing hearts (Vasan R S et al., Circulation 107: 1486-1491, 2003).

However, these previous studies often compare end-stage and drug-treated myocardium with normal myocardium. Therefore, the differences obtained may be secondary to failure and its treatment and such studies thus do not identify the factors that may lead to the failure of a compensated hypertrophied heart which may be used as a marker to identify patients at risk.

In the research that led to the present invention, the gene expression profile of a large number of genes from failing hypertophied hearts was compared with hypertrophied hearts that had remained compensated. Thus, genes were identified that were differentially expressed in failing versus compensated hypertrophied hearts. In particular, the present invention is based on the finding that particular non-myocytical genes are abnormally expressed in diseased heart tissue (Example 1 and 2).

According to the present invention use is made of non-myocytical markers. That is, markers that are derived from cells other than cardiac myocytes. This has the advantage that the method of the invention "probes" other processes than the known myoctic changes that occur in stressed myocytes. This opens the opportunity to not only diagnose heart failure, but also to continuously monitor patients with known heart failure, i.e. monitoring whether adverse non-myocytic processes (e.g. inflammation, scarring etc.) occur that may herald major adverse events.

According to the method of the present invention a biological sample is taken from an individual patient. Subsequently, the level of one or more markers in said sample is measured by well-known techniques. Typically, the level is compared with a standard level to determine whether the level of the marker is indicative of the potential of the individual to progress to heart failure. The standard level is based on the level of said marker in healthy subjects. If the level of the marker is elevated compared to the standard level, the subject is at risk for developing CHF or developing complications of heart failure.

The biological sample may be any sample of body fluid, such as blood, plasma, serum, urine etc., or tissue sample such as a cardiac biopsy. According to a preferred embodiment of the invention, however, the biological sample is a plasma sample derived from peripheral blood. Peripheral blood samples can easily be taken from the patients and do not need complex invasive procedures such as catheterization. The biological sample may be processed according to well-known techniques to prepare the sample for testing.

According to a preferred embodiment of the invention, the marker is a protein. The level of proteins can easily be determined by simple and reliable methods, such as immunological methods using specific antibodies against the proteins.

Preferably, the protein is galectin-3, as the level of galectin-3 has been demonstrated to be early and specifically expressed in failure-prone hearts.

According to another preferred embodiment of the invention, the protein is thrombospondin-2. It has been demonstrated that increased cardiac expression of TSP2 identifies those hypertrophied hearts that are prone to progress to overt heart failure.

The level of the markers may be determined by a any well-known suitable method. Preferably, the level of the marker is measured by an enzyme-linked immunosorbent assay (ELISA), thus providing a simple, reproducible and reliable method.

The present invention further relates to the use of one or more non-myocytical markers for identifying a subject at risk of developing hypertensive end organ damage, such as congestive heart failure. Several non-myocytical markers may be used according to the invention. Preferably, the marker is galectin-3, and/or thrombospondin-2.

The markers identified according to the present invention may further be used in the prevention and/or treatment of hypertensive end organ damage, in particular for the prevention and/or treatment of congestive heart failure. For example, inhibition of galectin-3 by for example antibodies, and/or activation of TSP-2 by suitable modulators may be beneficial for preventing the occurrence of heart failure. The present invention therefore further relates to the use of galectin-3 and/or modulators thereof for the manufacture of a medicament for the prevention and/or treatment of hypertensive end organ damage. The invention further relates to the use of thrombospondin-2 and/or modulators thereof for the manufacture of a medicament for the prevention and/or treatment of hypertensive end organ damage.

The present invention is further illustrated by the following Examples and Figures.

FIG. 1 is a flow-chart showing the steps for the implementation of previously reported statistical protocols and the comprehensive cutoff points for data mining. Multistep data filtering narrowed the numbers of differentially expressed genes in heart failure susceptible rats down to 49. HF-S, heart failure-susceptible rats; EST's, extended sequence tags.

FIG. 2 shows the results of real time PCR to quantify the expression of mRNA transcripts of four selected genes in myocardial biopsies taken from 10-week old rats, (a) TSP2 was significantly overexpressed in those rats that later progressed to rapid cardiac decompensation compared to those that remained compensated for the study period of 17 weeks, (b) Osteoactivin expression, (c) Collagen VI expression, (d) Expression level of brain natriuretic peptide. The data were normalized to the house keeping gene, cyclophilin. Comp, compensated; Decom, decompensated. *, $p<0.01$ compensated versus decompensated groups; #, $p<0.05$ SD versus Ren-2 rats; n=4 each group.

Figure 3:
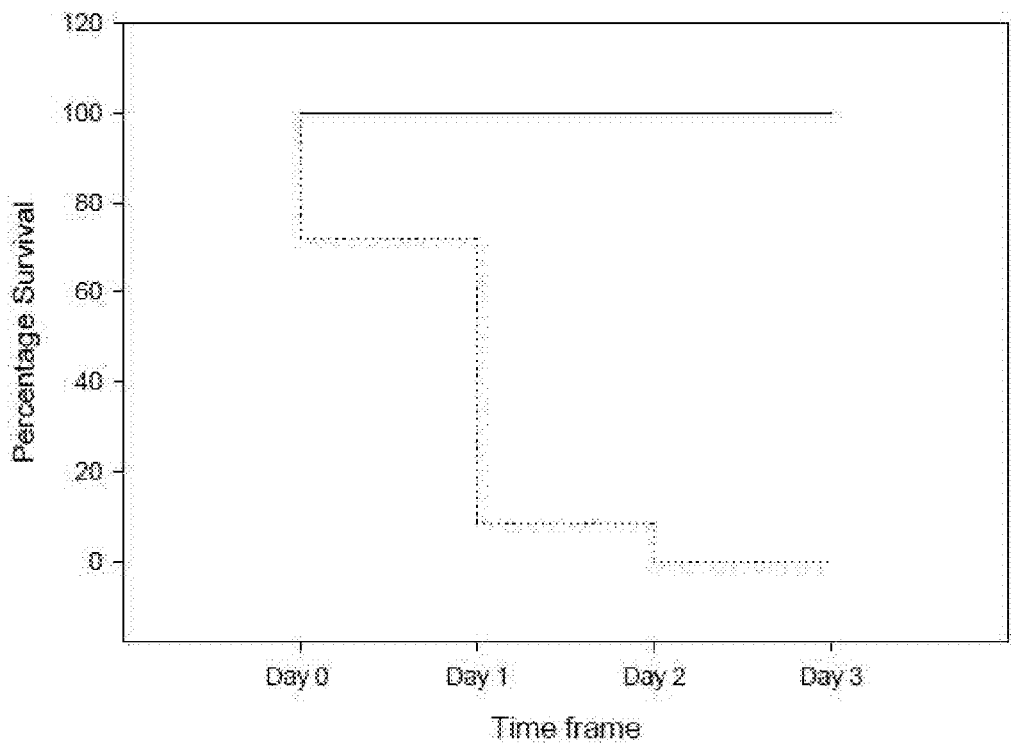

FIG. 3 shows the percentage survival of mice following induction of myocardial infarction. All the TSP2-null mice (dotted line) died within 72 hours after surgery (n=16). Excluding immediate postoperative death, no mortality was observed with wild-type (solid line) mice (n=22).

Figure 4:
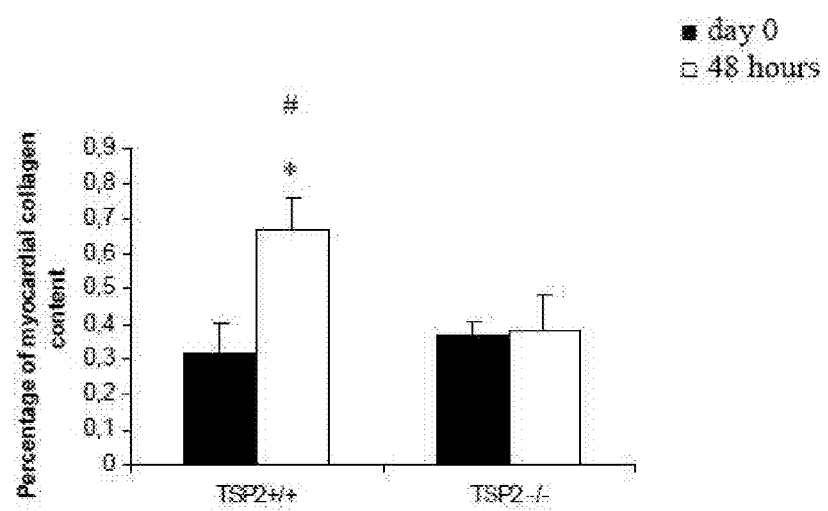
Figure 5A:
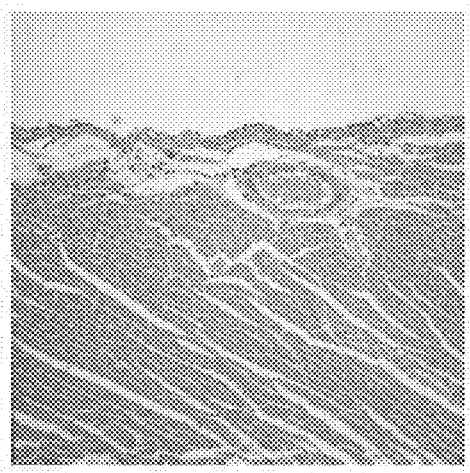
Figure 5B:
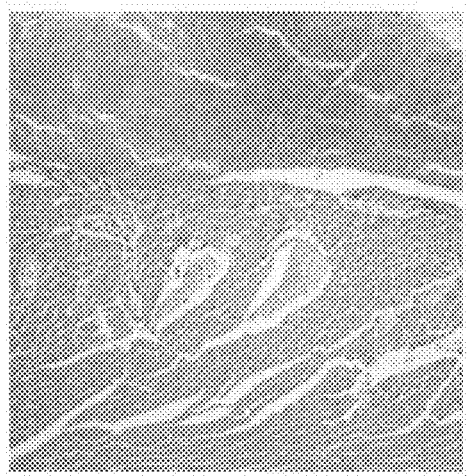
Figure 5C:
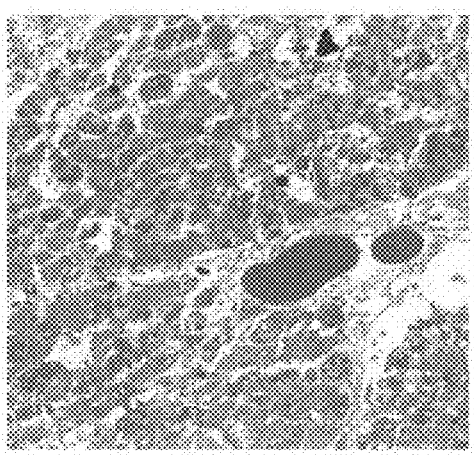
Figure 5D:
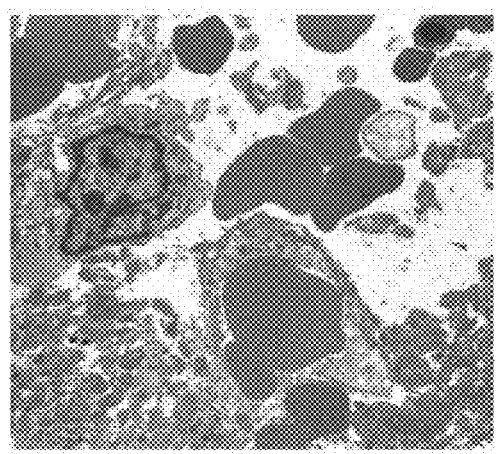

FIG. 4 is a bar diagram showing the results of the densitometric analysis of myocardial collagen content on day 0 and 48 hours post MI (10 random fields per section). TSP2-null mice failed to mount a reactive fibrosis 48 hours after MI compared to wild-type mice. *, $p<0.01$, wild-type vs null strains 48 hours post MI; #, $p<0.01$, day 0 vs 48 hours post MI in wild-type mice.

FIG. 5 shows photo- and electron micrographs of the infarcted left ventricular wall. Haematoxyline/Eosin stained section showing intact matrix around the blood vessel with no evidence of interstitial haemorrhage in wild type mice (a). Extensive tissue destruction and interstitial bleeding (*) in $TSP^{-/-}$ mice (b). Electron micrographs from the infarcted left ventricular wall (wild-type strain) (c). Note relatively well maintained vascular and matrix architecture. Sections from TSP2-null mice showed widespread damage of the myocardial matrix and haemorrhage (*) in interstitial areas (d).

Figure 6A:
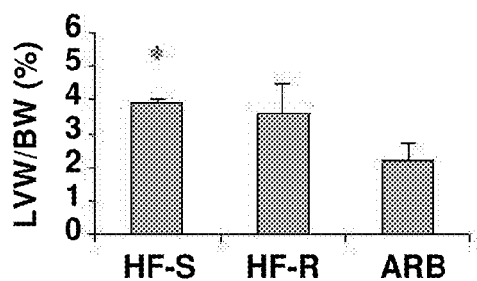
Figure 6B:
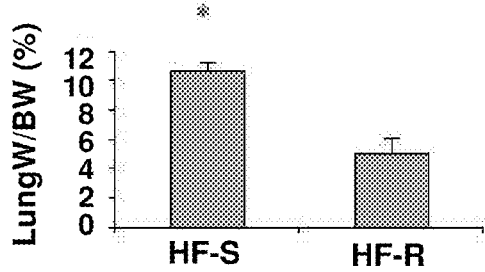
Figure 6C:
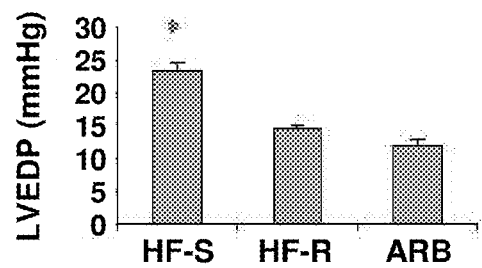

FIG. 6 shows the haemodynamic parameters of HF-S, HF-R and ARB treated rats. Haemodynamic assessment of Ren-2 transgenic rats with and without ARB (0.05 mg/kg/day candesartan from 7-11 weeks) administration. A, LVW/BW (%), a representative measurement of left ventricular hypertrophy. B, LW/BW(%), indicated the development of congestive heart failure and, C, LVEDP shows the extent of diastolic dysfunction. Both HF-S and HF-R animals had left ventricular hypertrophy. High fibrosis-score animals had higher LW/BW and LVEDP. The parameters were measured before the sacrifice. N=4 each for HF-S and HF-R and 8 for ARB. *, $P<0.05$ in HF-S vs HF-R and ARB.

Figure 7:
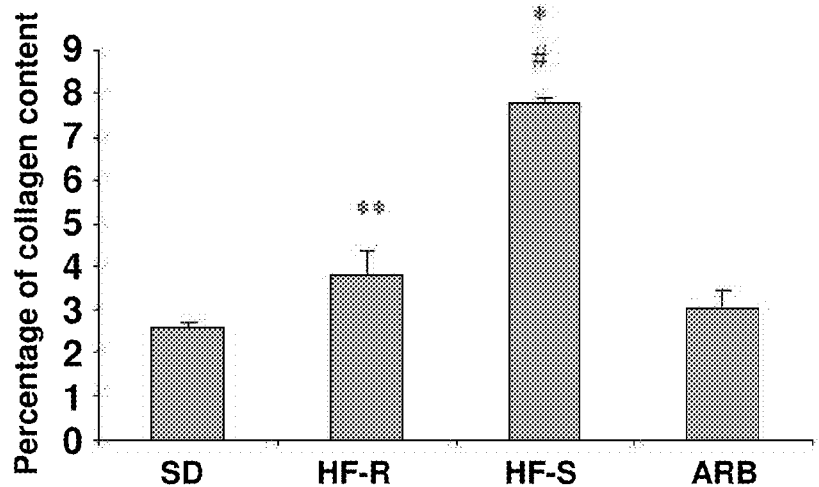

FIG. 7 shows the results of left ventricular collagen volume fraction analysis of picrosirius red stained sections of rat myocardium. The bar diagram shows the quantification of LV interstitial collagen. 1, control; 2, HF-R; 3, HF-S; 4, ARB. N=4-6 each group; #, $P<0.01$ vs control; *, $P<0.05$ HF-S vs HF-R; **, $P<0.05$ in HF-R vs SD.

Figure 8A:
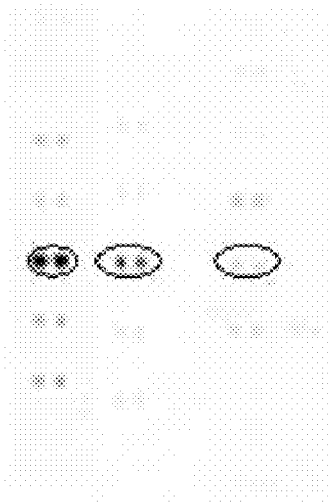
Figure 8B:
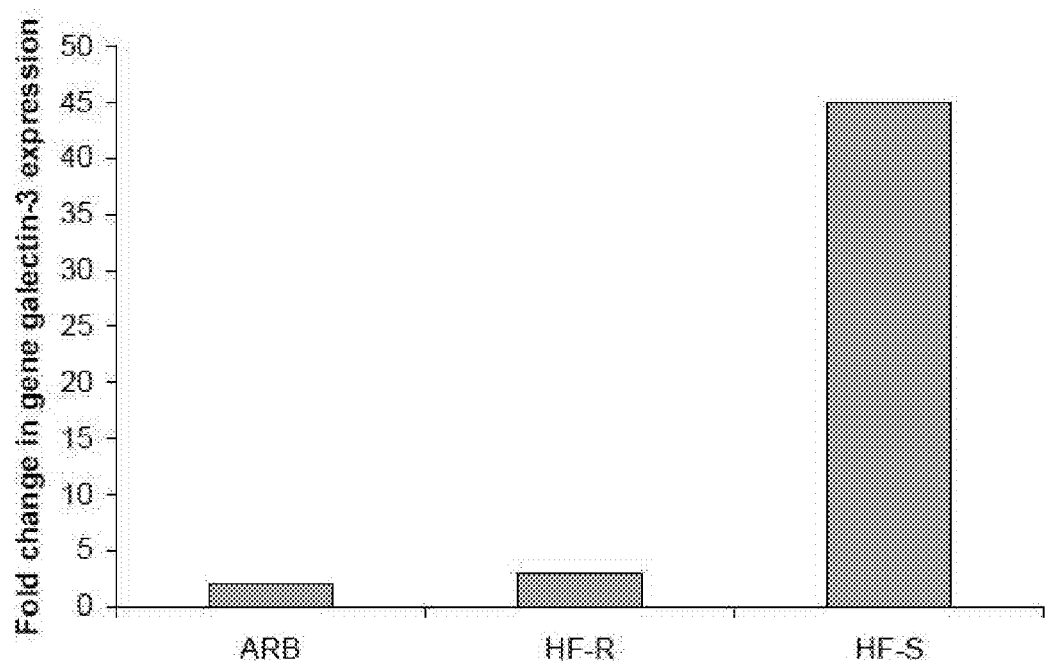
Figure 10A:
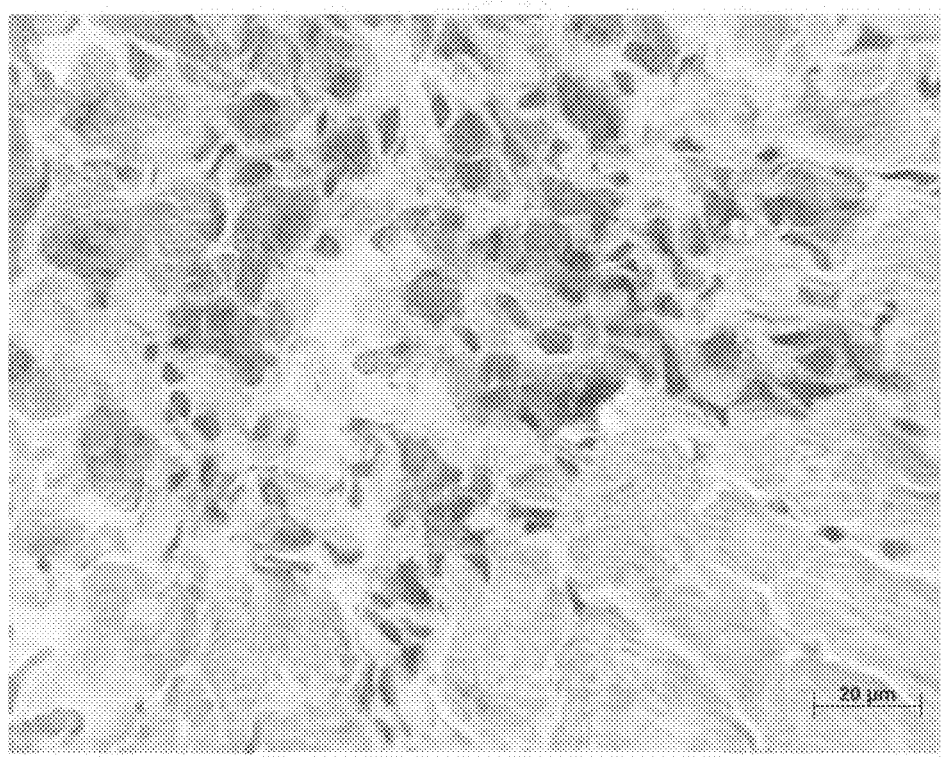
Figure 10B:
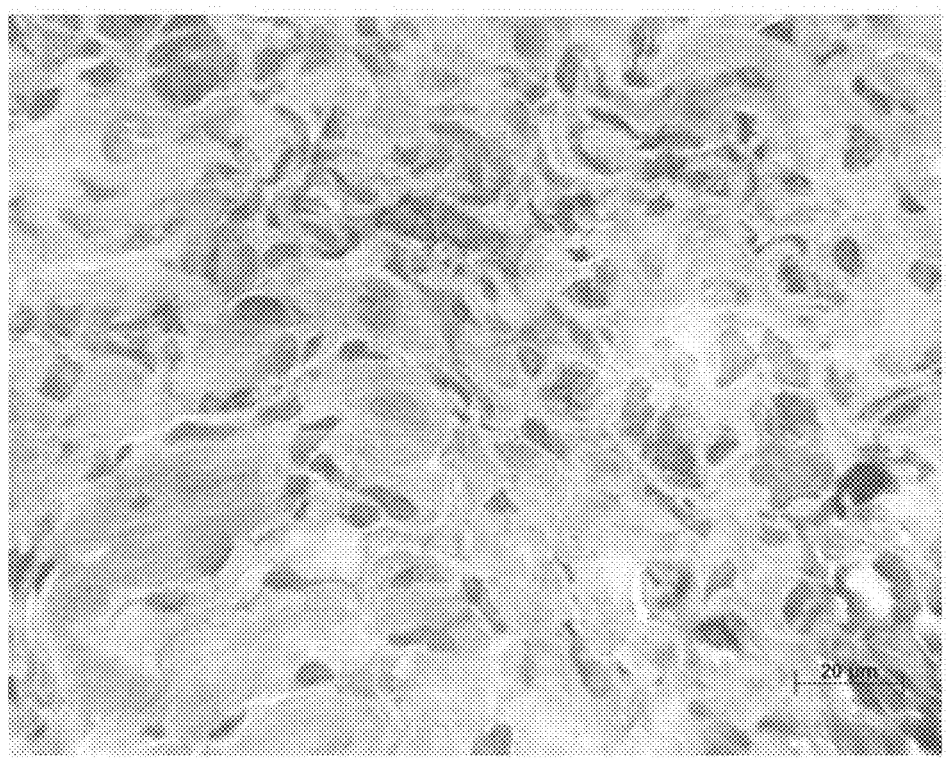
Figure 10C:
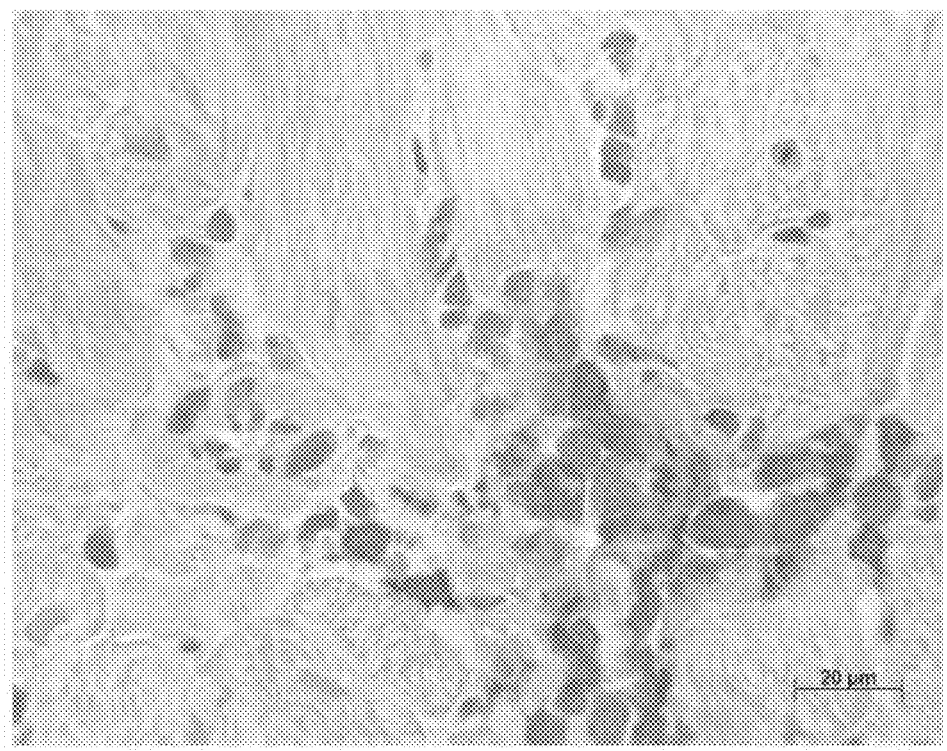
Figure 10D:
Figure 10E:
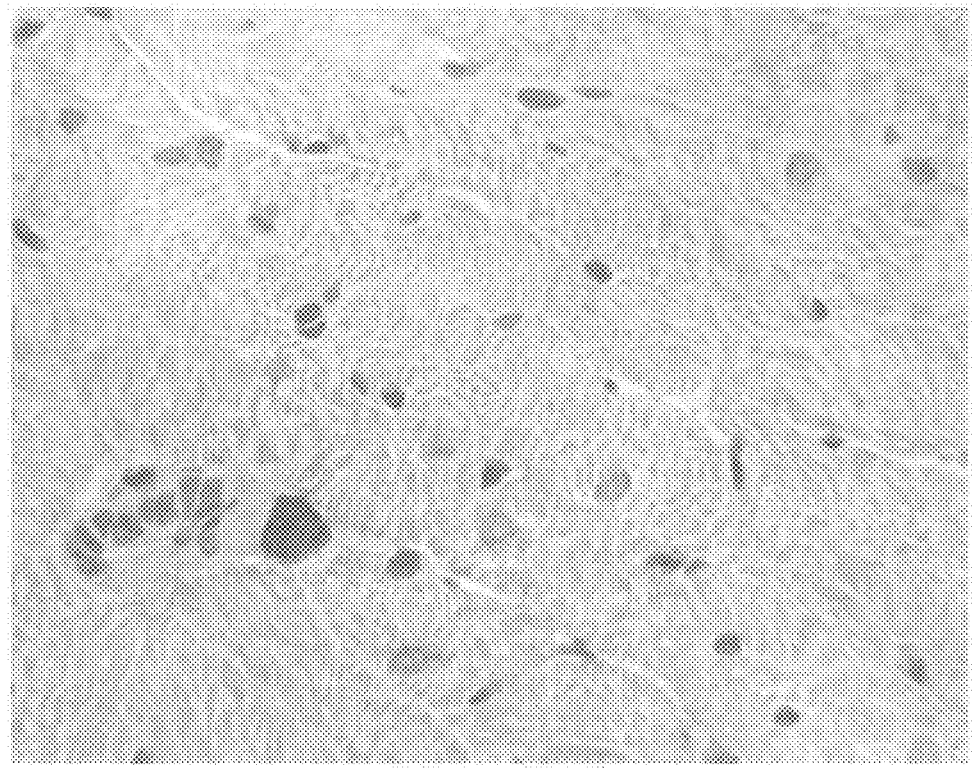
Figure 10F:
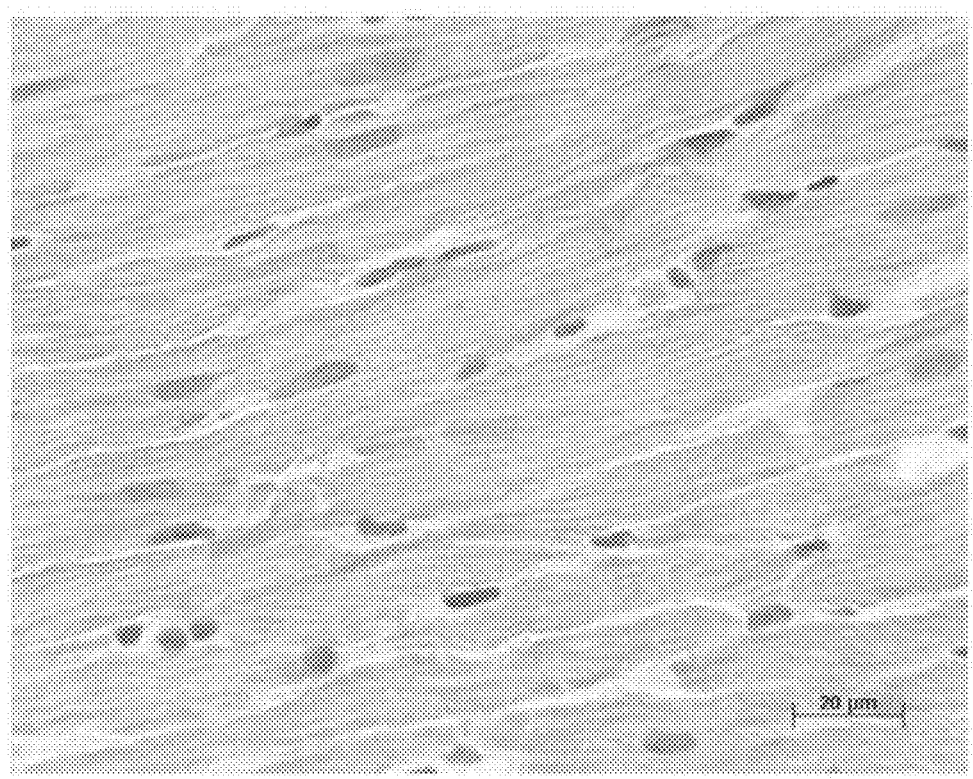

FIG. 8 shows a dot blot of differentially expressed genes in Ren-2 rats. Galectin-3 mRNA level was compared among HF-S, HF-R and ARB treated group of rats. Density and diameter of the dots corresponds directly to the level of gene expression compared to SD controls. A, Phsopho-imager scanned images from HF-S, HF-R and ARB treated rats respectively. The circled dots represent galectin-3 mRNA expression. B, Bar diagram showing the amount of galectin-3 quantified in densitometric units. N=2, each group and each sample was spotted in duplicates.

FIG. 9. Immunoblot for galectin-3, cyclin D1 and E2F-1. Expression levels in rat myocardial homogenates of galectin-3: A1, representative blot; A2, quantification in densitometric units normalized to GAPDH; cyclin D1:B1, representative blot; B2, quantification in densitometric units normalized to GAPDH.

FIG. 10 demonstrates the immunohistochemical co-localization of galectin-3, macrophages and MHC-II. Parallel sections obtained from the myocardium of HF-S rats stained with A, anti-galectin-3 mouse monoclonal antibody counter-stained with hematoxyline; B, macrophage specific anti-CD68 mouse monoclonal antibody; C, OX-6 mouse monoclonal antibody against MHC-II antigen. A different microscopic field showing dense infiltration of macrophages, D. Macrophage infiltration in HF-R animals was sparsely seen (E), and well preserved myocardial morphology in SD controls, F.

Figure 11A:
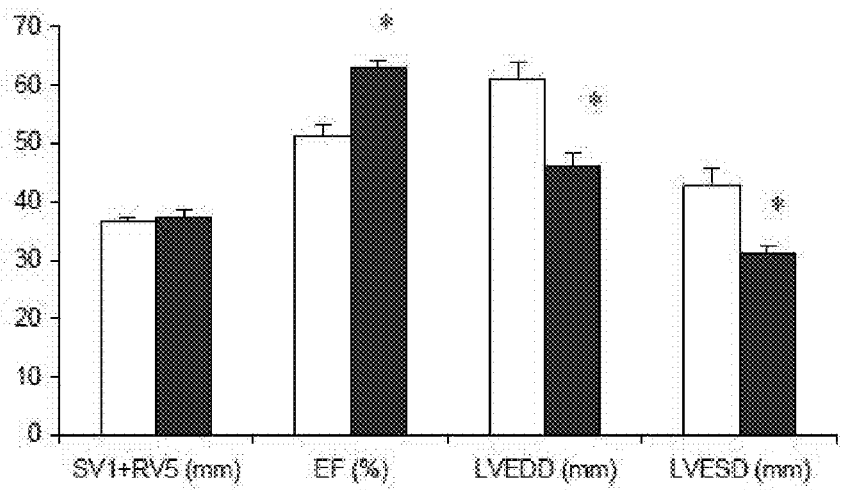
Figure 11B:
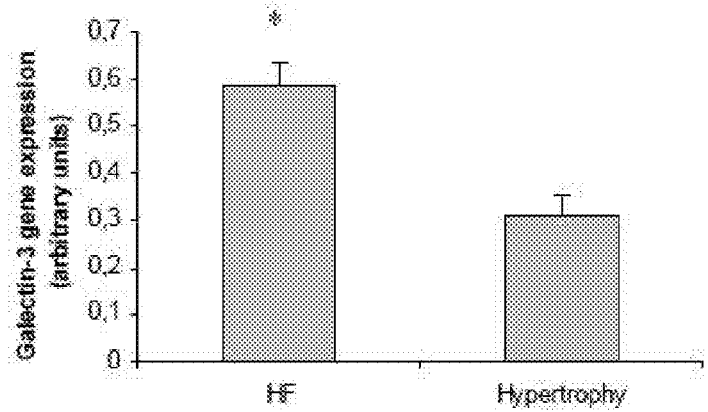

FIG. 11. Electro- and Echocardiographic assessment of LVH and HF in human subjects and quantitative real-time PCR to assess myocardial galectin-3 gene expression.

A, Left ventricular hypertrophy assessed by Skowlow and Lyon criteria (SV1+RV5>35 mm). EF of less than 55% is considered a decompensated state. B, Real-time PCR using human galectin-3 probe. Galectin-3 gene expression profiled in human myocardial biopsies. The results were normalized to house-keeping gene, cyclophilin. N=6, *, P<0.05 HF vs LVH.

Figure 12:
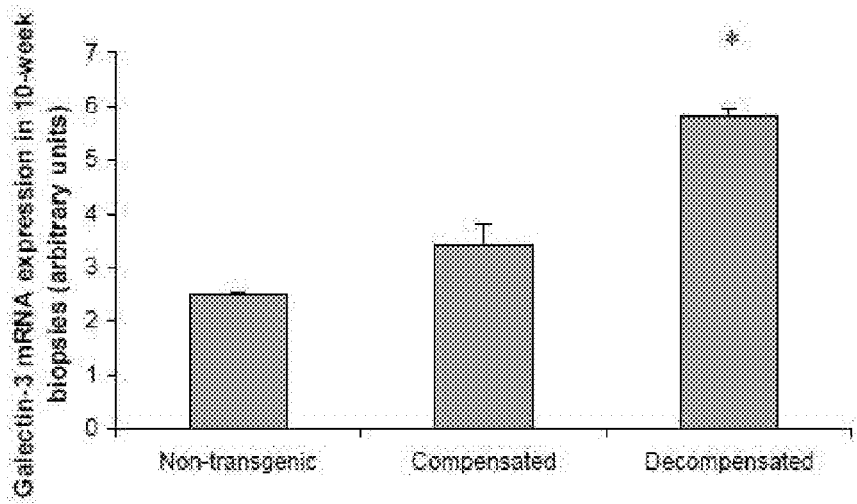

FIG. 12 shows galectin-3 mRNA expression in 10-week biopsies.

EXAMPLES

Example 1

Thrombospondin-2

Increased Expression Identifies Failure-prone Cardiac Hypertrophy

Cardiac hypertrophy increases the risk of heart failure (HF), but, so far, it has been is difficult to predict which hypertrophied myocardium will progress rapidly to HF. According to the present invention it was reasoned that, apart from hypertrophy-related genes, distinct failure-related genes are expressed before failure is apparent, thus permitting molecular prediction of hypertrophied hearts liable to fail. Cardiac gene expression (12,336 clones) of hypertensive homozygous renin-overexpressing (Ren-2) rats that progressed to HF at 12-14 weeks of age, were compared with expression by littermates that remained compensated for 17 weeks. Cardiac biopsies taken at the stage of compensated hypertrophy (10 weeks of age) allowed the inventors to test whether altered expression of identified genes preceded later progression to HF. 49 genes that were overexpressed in the myocardium of HF rats were identified, of which matrix genes comprised the largest group. Thrombospondin-2 (TSP2) was selectively overexpressed only in biopsies from rats that later progressed to HF, while brain natriuretic peptide (BNP) was, at this early stage, elevated in all rats. To test the effects of absence of TSP2 on the cardiac matrix, myocardial infarction (MI) was induced in TSP2-null mice; this procedure resulted in cardiac rupture in all TSP2-null mice, but in none of the wild type (WT) mice. In conclusion, TSP2 was identified as a novel and crucial regulator of the integrity of cardiac matrix.

Materials and Methods

Transgenic Rats and Hemodynamic Studies

Homozygous Ren-2 rats were obtained from the Max-Delbrück-Zentrum für Molekulare Medizin, Berlin, Germany. 30 male Ren-2 rats on a Sprague Dawley (SD) background and 9 age-matched SD rats as controls were studied. Of 30 Ren-2 rats, 8 were sacrificed at 10-weeks of age and 8 were treated with 0.05 mg/kg/day of candesartan, an angiotensin II receptor type I blocker (ARB), from 7-13 weeks of age. Of the remaining 14 untreated Ren-2 rats, 6 were sacrificed at 13 weeks upon the development of clinical signs of heart failure and designated as HF-S rats. The remaining 8 Ren-2 rats were closely monitored and were sacrificed at 17 weeks when clinical signs of failure had not yet appeared. These rats were designated as HF-R rats. Hemodynamic parameters were determined before sacrifice and heart, lung and body weight were measured after the sacrifice. The procedure for care and treatment of animals was approved by the institutional animal care committee.

Biopsies from 10-Week Ren-2 Rats

A second group of 12 Ren-2 and 4 SD rats were anesthetized and the anterior thorax was shaved at the sternum. The rats were fixed to a hard board on top of a warming pad with the help of self-made loops. A blunt 20-gauge needle was placed in the trachea to serve as a tracheal cannula. The cannula was connected to a volume-cycled rodent respirator (model 683, Harvard Apparatus, South Natick, Mass.) on room air with a tidal volume of 2.5 to 3 ml and respiratory rate of 80 breaths/min. Further procedures were done with visual help of a micro-dissecting microscope. A 5 mm incision at the left $4^{th}$ intercostal space was made to access the thorax. After having a clear view of the heart, a biopsy was taken using a custom-made 0.35 mm needle connected to a slowly rotating drill. The whole procedure lasted approximately 15 minutes. Of the 9 Ren-2 rats that survived the operation, 5 developed heart failure between 12-14 weeks of age whereas the remaining four rats stayed compensated until 17 weeks.

RNA Isolation and Reverse Transcription

RNA was isolated from left ventricles with an RNeasy Mini Kit, following the RNeasy Mini Protocol (QIAGEN, Hilden, Germany), and stored at −80° C. The quality of the extract was measured using the Eukaryote Total RNA nano-assay in a 2100 Bioanalyser (Agilent Technologies, Amstelveen, The Netherlands). RNA was isolated from 10-week rat heart biopsies with the PicoPure RNA Isolation Kit (Arcturus, CA, USA), according to manufacturer's instructions. The RNA was transcribed into cDNA with reverse transcriptase, using 250 ng of random primers (Invitrogen Life Technologies, Breda, The Netherlands).

cDNA Microarrays cDNA clones isolated from a normalized rat cDNA library were chosen for analysis on microarrays using an Incyte GEM-2/GEM-3 rat cDNA library (total 12,336 genes). PCR-amplified inserts of each cDNA were printed as high-density arrays on treated glass surfaces. Duplicate hybridizations were performed on these array elements with two SD and six Ren-2 rat myocardial mRNAs at 3 different time points. Log transformation of the values was done in order to homogenize the data, and only differences in expression of >1.7 fold were considered differentially expressed. The protocol for data mining and validation was adopted, as detailed previously (Tan et al., Proc Natl Acad. Sci. 99: 11387-11392, 2002; Bandman et al., Ann NY Acad. Sci., 975: 77-90, 2002).

Sequencing, membrane spotting, and cDNA hybridization for macroarray

Clones of the differentially expressed genes identified by microarray were obtained from Incyte genomics and sequenced with a 5'-GGTGACACTATAGAAGAGC-3' (SEQ ID NO: 1) primer (Eurogentec, Seraing, Belgium). After confirming the identity by sequencing, the plasmid inserts were amplified by a PCR reaction with 5'-ACCATGATTACGC-CAAGCTC-3'(SEQ ID NO: 2) and 3'-ACGACGGCCAGT-GAATTGAA-5' (SEQ ID NO: 3) primers. Each clone was then spotted in duplicate on nylon membranes (macroarray). The dot blots were scanned with a personal fx-phospho imager (Cyclone System Packard, Meriden, CO, USA). Individual hybridization signals were identified and quantified densitometrically using Quantity One, Version 4.2.3 software (BioRad, Munich, Germany). Glyceraldehyde-3-phosphate dehydrogenase (GAPDH) was selected as a housekeeping gene for internal normalization of the blots.

Bioinformatic Analysis

Bioinformatic analysis of the protein sequences translated from 49 HF-specific candidate genes, selected from microarray analysis and multi-step data-mining strategy, was performed. Based on the annotations of their biological functions, three candidate genes, previously not identified in myocardium, and that encode matrix-related proteins, were chosen for further testing by real time PCR.

Primers, Probes and Real-time PCR

Primers and probes were designed from rat sequences available in GenBank™ using Primer Express Software (PE Applied Biosystems, Foster City, Calif., USA). Probes were designed from conserved exon splice sites derived from the Ensembl-Mouse Genome Sequencing Consortium and Ensembl-Human Genome Browser, thus preventing recognition by the assay of any potentially contaminating genomic DNA (Table 1). Optimal PCR conditions were found to be 12.5 ml 2×PCR Master Mix for Taqman™ assays, with a final concentration of 5 mM $MgCl_2$, 300 nM of each primer, 200 nM probe, and 10 ng cDNA-template in a total volume of 25 ml. Amplification and detection were carried out using the ABI Prism 7700 Sequence Detection System (PE Applied Biosystems, Foster City, Calif., USA). The PCR data were reported relative to the expression level of the housekeeping gene, cyclophilin A.

Experimental MI and Morphometry in $TSP2^{-/-}$ Mice

Myocardial infarction was induced in 22 wild-type (129 SvJ strain) and 16 TSP2— null mutant ($TSP2^{-/-}$) mice by occluding the left anterior descending coronary artery. Two sham-operated mice were used as controls. These mice were killed, after ether anesthesia, by injecting 1 ml 0.1 M $CdCl_2$ into the vena cava. The heart was perfusion-fixed with 5% buffered formalin for 10 minutes and immersion-fixed overnight in 10% buffered formalin. Tissue specimens of wild-type and $TSP2^{-/-}$ mice were evaluated using standard electron microscopical techniques. To quantify the extent of fibrosis, computerized planimetry was performed in seven randomly selected fields per section. Each field represented a 400 μm² area. Collagen area was quantified selectively from left ventricular interstitium excluding perivascular and epicardial collagen. Collagen area fraction was calculated as the ratio of area stained by picrosirius-red to total myocardial area per field. The details of the procedure have been reported previously (Cherayil et al., Proc Natl Acad Sci USA, 87: 7324-7328, 1990; Cleutjens et al., Am J pathol., 147: 325-338, 1995).

Statistical Analyses

Data are presented as mean±SEM. The data for each study group (candesartan-treated and two groups of untreated renin-transgenic rats) were compared using one-way analysis of variances (ANOVA) in combination with a Dunnett post-hoc analysis to correct for multiple comparisons. SD rats were used as an internal control cohort. Analyses were performed using the statistical package SPSS 10.0 (Chicago, Ill., USA). $P$-values<0.05 were considered to be statistically significant.

Results

Rapid Transition to Overt Heart Failure and Death in a Subset of Ren-2 Rats

Hypertrophied left and right ventricles were noticed in the 8 rats that were sacrificed at 10 weeks and also in other untreated rats that were sacrificed at later dates. No LVH was noticed in SD controls. Six out of 14 Ren-2 rats on placebo rapidly transited towards overt clinical HF between 12 to 14 weeks of age and had depressed cardiac functional indices compared to the 8 rats that remained compensated throughout the observation period of 17 weeks. Pleural effusion and sharp fall in $dP/dt_{max}$ were noted in HF-S rats; these changes were not apparent in HF-R rats (Table 2). Angiotensin II blockade completely prevented the development of cardiac hypertrophy and failure (LV weight/body weight %, 2.52±0.36, $dP/dt_{max}$, 8400±202) when evaluated in sacrificed animals at 13 weeks.

Microarray Revealed 49 Genes Overexpressed in Heart Failure Susceptible Rats.

For microarray analysis, we first examined biological variability in gene expression between HF-S and HF-R groups. The expression levels of most genes in the two HF-S and HF-R groups were very similar. Out of a total of 12,336 genes profiled for expression, only 49 genes survived the multi-step data mining strategy (FIG. 1) and were overexpressed in HF-S rats. Nicotinamide adenine dinucleotide (NAD) transhydrogenase was the only gene with reduced expression in failing myocardium. Notably, expression of osteoactivin, TSP2, several pro-collagens and thrombospondin-1 were increased. Many of the identified genes encode proteins with known functions whereas others correspond to genes of unknown function, including novel genes and genes not previously detected in the heart.

Bioinformatic analysis pointed to three novel cardiac matrix-related genes

Since no information was available as to the function of many of the overexpressed genes in HF, we subjected all the 49 genes to bioinformatic analysis. Initially, we made a broad functional classification of the HF susceptibility genes using GeneFIND (Gene Family Identification Network Design) System, which combines several search/alignment tools to provide rapid and accurate gene family. This strategy indicated that most of the overexpressed genes encode matrix-related proteins. Notably, the functions of 3 selected susceptibility genes (osteoactivin, thrombospondin-2 and collagen VI) were not previously reported in the myocardium.

Macroarray Showed Normalization of HF Susceptibility Genes by Angiotensin II Blockade To confirm the role of the renin-angiotensin system (RAS) activation in this angiotensin-driven model of heart failure, we re-assessed the expression of the target genes identified by microarray after treating a subgroup of Ren-2 rats with a sub-pressor dose of candesartan from 7 to 13 weeks of age. In addition to improving the hemodynamics, ARE treatment prevented the overexpression of all HF-related candidate genes (data not shown).

Figure 2A:
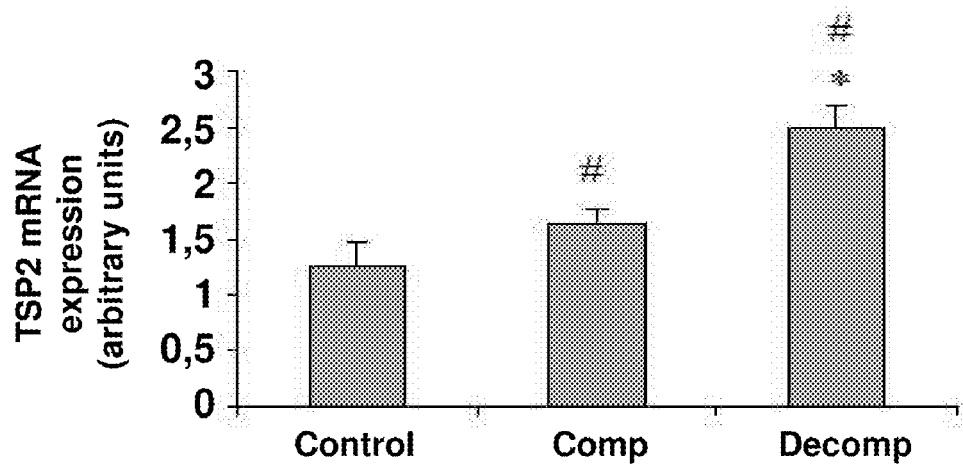
Figure 2B:
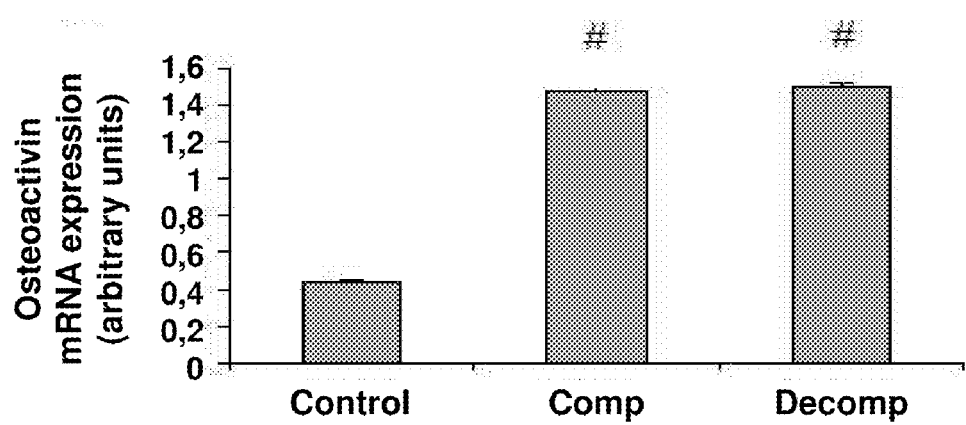
Figure 2C:
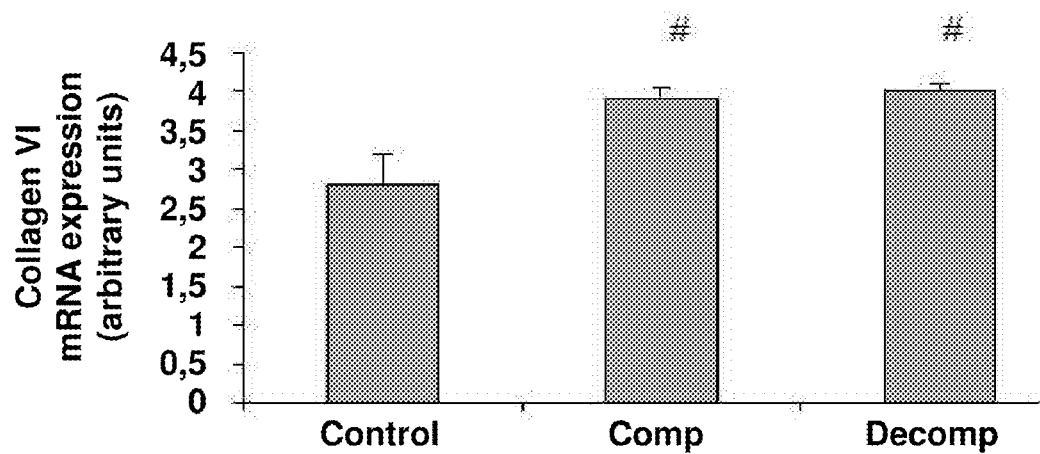
Figure 2D:
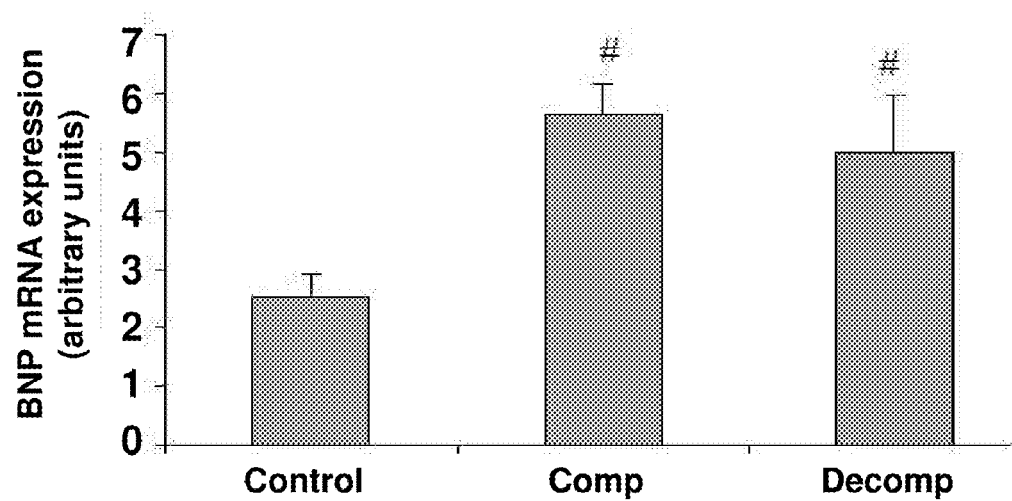

Myocardial Biopsy at 10 Weeks Showed TSP-2 Upregulation in Rats that Later Rapidly Progressed to HF To evaluate the expression status of the 3 matrix-related genes in the myocardium before HF became hemodynamically and clinically apparent, we developed a technique to obtain cardiac biopsies in the spontaneously beating rat heart. After biopsy, the rat was allowed to recover to determine whether it would prove to be resistant or susceptible to heart failure. This novel approach allowed us to establish the levels of gene expression before failure became apparent. TSP2 expression was significantly increased at the early hypertrophy stage (10 weeks) only in those rats that developed rapid cardiac decompensation within 12-14 weeks (FIG. 2a), while it was not upregulated at this stage in the rats that subsequently remained compensated, nor in non-transgenic control rat hearts. Expression levels of other HF related candidate genes, such as osteoactivin (FIG. 2b) and collagen VI (FIG. 2c), were increased in the early hypertrophy stage both in the rats that later failed, and in those that remained compensated compared to controls. Importantly, the widely used marker of cardiac hypertrophy and failure, was upregulated in the 10-week biopsy in all rats irrespective of later compensation or failure and could therefore not distinguish failure-prone from failure-resistant rats (FIG. 2d). In accordance with our initial microarray studies, expression of these 3 genes further increased to more than 2-fold of their 10-week expression levels upon the development of heart failure. Compensated rats, despite having high osteoactivin, collagen VI, and ENP at 10 weeks, had no further significant increase in the expression levels of these genes upon the sacrifice at 17 weeks (data not shown).

TSP-2 Knock Out (TSP$^{-/-}$) Mice Cannot Survive Acute Myocardial Infarction

In contrast to various rat models of heart failure, there are no carefully documented mouse models that consistently develop heart failure in response to pressure overload. Therefore, we infarcted the anterior myocardium in 22 wild-type and 16 TSP2$^{-/-}$ mice to address the biological role of TSP2 in acute myocardial structural damage and consequently, rapid cardiac remodelling. Infarction was not tolerated by TSP2-null mice, since all mice died from cardiac rupture within the first 72 hours after MI. On the other hand, 100% of the wild-type mice that did not succumb to immediate post-operative complications survived (FIG. 3). Computerized morphometry, 48 hours post-MI, showed an apparent complete lack of reactive increase in myocardial collagen in TSP2-null compared to wild-type mice (0.38±0.05% and 0.70±0.04%, respectively; $p<0.05$) (FIG. 4). Light and electron microscopy revealed extensive disruption of myocardial matrix in TSP2-null mice. None of the wild-type mice demonstrated this phenotype (FIG. 5).

Discussion

It was demonstrated in this study that increased cardiac expression of TSP2 identifies those hypertrophied hearts that are prone to progress to overt heart failure. It was further shown that TSP2 is required to mount an effective response to acute cardiac loading. In contrast, known markers of hypertrophy like BNP were invariably increased in all forms of cardiac hypertrophy and therefore could not distinguish between failure-prone and failure-resistant forms of hypertrophy.

Although the family of thrombospondins has been studied extensively in vascular and thrombotic diseases, there are no reports that substantiate an important role for thrombospondins in heart failure. Our findings suggest that TSP2 may perform, directly or indirectly, a crucial function in cardiac matrix biology.

TSP2 is a secreted matricellular glycoprotein whose functions are diverse and incompletely understood. Since no close orthologues of TSP2 were found in the genomes of *Caenorhabditis elegans* or *Drosophila*, it appears that this protein has evolved to cope with the increased complexity of cell-matrix interaction in vertebrates. As evidence for a role of TSP2 in the organization of the extracellular matrix, previous studies in TSP2-null mice have shown that loss of TSP2 expression results in abnormally large collagen fibrils with irregular contours. Furthermore, the skin of TSP2—null mice is fragile and has reduced tensile strength. TSP2-null skin fibroblasts are defective in their attachment to a substratum and have increased levels of matrix metalloproteinase-2 (MMP-2) in their culture. The current study has identified two, apparently contradictory, functions for TSP2 in the myocardium. In chronic hypertension in Ren-2 rats, increased cardiac expression of TSP2 identifies those animals that are prone to heart failure. While this response would appear to indicate that expression of TSP2 is detrimental, it is likely that the response reflects a heightened, previously activated, injury response in rats that later progress to overt failure, in comparison with the response in rats that remained compensated for a prolonged period of time. It is well established that the expression of TSP2 is characteristic of the response to injury in adult animals. On the other hand in experimental myocardial infarction in mice, the presence of TSP2 clearly protects against cardiac rupture. While the two experimental systems are difficult to compare because different species are involved and, in the case of TSP2-null mice, complex compensatory changes are likely to be present, both sets of results are consistent with an important role for TSP2 in generating a fully functional extracellular matrix after an injury. In the case of excisional skin wound healing in TSP2-null mice, the absence of TSP2 appears to be beneficial because in this particular form of wound healing the resulting increase in angiogenesis and in MMP2 accelerate healing, despite the pre-existing structural changes in collagen fibers that are known to be present in this tissue. However, it is suggested that the prior intrinsic weakness of cardiac tissue, due to similar abnormalities in the matrix of the myocardium, predispose to cardiac rupture after infarction.

The present data suggest that increased cardiac expression of TSP2 precedes progression to failure. Since it is known that thrombospondins can bind to integrins it is possible that TSP2 mediates pro-fibrotic effects via integrin signaling. Recently Zhang et al. (J Clin Invest 111: 833-841, 2003) reported that mice with haploinsufficiency of the adaptor protein gene, Grb2, are resistant to cardiac fibrosis in response to pressure overload. Grb2 is recruited in integrin-mediated activation of focal adhesion kinase that can result from mechanical stress. In our study we found that $\beta 1$ integrin was among the genes whose expression was clearly increased in the hearts of hypertensive Ren2 rats and was further increased in failing hearts. This finding was substantiated by our recent observation that the stretching of cardiac fibroblasts in vitro increased protein levels of $\beta 1$ integrin (S. Pokharel and Y. M. Pinto, unpublished data).

It should be noted that the picrosirius red staining technique for quantification of collagen relies on the size, alignment, and packing of collagen fibres to show visible polarization of orange-red colour. Since TSP2-null mice have an abnormal collagen fibril and fiber structure, specifically less organized fibers and irregular and larger fibrils, the birefringence that was measured could have been affected by these changes.

In conclusion, according to the present invention it is proposed that TSP2 functions as a crucial regulator of the integrity of the cardiac matrix. Since increased extracellular matrix formation characterizes both experimental and clinical forms of pressure overload-induced heart failure, the early expression of TSP2 may reflect a matrix response that is crucial in the transition from compensated hypertrophy to heart failure. These observations show that early detection of cardiac over-expression of TSP2 can identify those hypertrophied hearts that are susceptible to heart failure, and may facilitate early identification and possibly treatment of patients that are prone to progress to heart failure.

Example 2

Galectin-3 Marks Activated Macrophages in Hypertrophied Hearts Prone to Failure

The increased myocardial expression of macrophage chemoattractant proteins and various cytokines has suggested that macrophages are involved in heart failure (HF). However, it is unclear whether macrophages merely respond to already established injury, or are actively involved in the early stages of HF. To study these mechanisms in hypertensive HF, the inventors employed homozygous hypertensive TGR(mRen2) 27 (Ren-2) rats. These rats invariably develop cardiac hypertrophy by the age of 10 weeks, whereafter some remain compensated up to 17 weeks, while others progress to failure and death around age 12-14 weeks. This study shows that cardiac galectin-3 expression specifically marks hypertrophied hearts prone to progress to failure. Macrophages appear to be activated early and specifically in failure prone hypertrophied hearts and macrophage derived mediators like galectin-3 may contribute to the development of cardiac fibrosis and progression towards HF.

Materials and Methods

Transgenic Rats and Hemodynamic Studies

Homozygous Ren-2 rats were obtained from the Max-Delbrück-Zentrum für Molekulare Medizin, Berlin, Germany. We studied 16 male Ren-2 rats and 8 age-matched controls from the non-transgenic background, Sprague Dawley (SD) rats. Of the 16 Ren-2 rats, 8 were treated with 0.05 mg/kg/day of candesartan, an angiotensin II receptor type I blocker (ARB), from 7-13 weeks of age. Within 8 untreated Ren-2 rats, 4 were sacrificed at 13 weeks upon the development of HF. The remaining 4 Ren-2 rats were monitored and were sacrificed at 17 weeks when signs of clinical failure had not appeared. Hemodynamics was taken at 10 weeks and before sacrifice. Heart, lung and body weight were measured after the sacrifice. The procedure for care and treatment of animals was approved by the institutional animal care committee.

Myocardial Biopsies from 10-Week Ren-2 Rats

A second group of 12 Ren-2 and 4 SD rats were anesthetized and a blunt 20-gauge needle was placed in the trachea to serve as a tracheal cannula, which was connected to a volume-cycled rodent respirator (model 683, Harvard Apparatus, South Natick, Mass.) on room air with a tidal volume of 2.5 to 3 ml and respiratory rate of 80 breaths/min. With the visual help of a micro-dissecting microscope, a 5 mm incision at the left $4^{th}$ intercostal space was made to access the thorax. Biopsy was taken using a custom-made 0.35 mm needle.

cDNA Microarrays cDNA clones isolated from a normalized rat cDNA library (total 12,336 genes) were chosen for analysis on microarrays (Incyte Genomics, CA, USA, rat GEM-2/3). PCR amplified inserts of each cDNA were printed as high-density array on glass surfaces. Duplicate hybridizations were performed on these glass chips with two SD and six Ren-2 rat myocardial mRNA at three different time points. The target genes that showed statistically significant (P<0.001) changes in expression with at least 2-fold overexpression in HF-S group were reprinted onto a sub-array for further analysis so that the genes were independently assessed four times to improve the level of reliability. The protocol for data mining (Tan F L et al., Proc Natl Acad. Sci., 99: 11387-11392, 2002) and validation was adopted, as detailed previously (Bandman O et al., Ann NY Acad. Sci. 975: 77-90, 2002).

Primers and probes

Primers (forward, 5'-CCCGACTGGACCACTGACA-3' (SEQ ID NO: 4), reverse, 5'-CAGCATGCGAGGCATGACT-3' (SEQ ID NO: 5) and probe, 5'-TGCCCTACGATATGC-CCTTGCCTG-3' (SEQ ID NO: 6)) specific to galectin-3 were designed from sequences available in GenBank™ using Primer Express Software (PE Applied Biosystems, Foster City, CA, USA).

RNA Isolation and Real Time PCR

RNA was isolated from rat left ventricle with the RNeasy Mini Kit following the RNeasy Mini Protocol (QIAGEN, Hilden, Germany) and stored at −80° C. RNA was isolated from rat heart biopsies with the PicoPure RNA Isolation Kit (Arcturus, CA, USA) according to manufacturer's instructions. Optimal PCR conditions were found to be 12.5 µm 2×PCR Master Mix for Taqman™ assays with final concentration of mM $MgCl_2$, 300 nM of each primer, 200 nM probe and 10 ng cDNA-template in a total volume of 25 µl.

Sequencing, membrane spotting and cDNA hybridization for macroarray

Clones of the differentially expressed genes identified by microarray were obtained from Incyte genomics and sequenced with 5'-GGTGACACTATAGAAGAGC-3' (SEQ ID NO: 7) primer (Eurogentec, Seraing, Belgium). After confirming the identity, the plasmid inserts were amplified by PCR reaction with the 5'-ACCATGATTACGCCAAGCTC-3' (SEQ ID NO: 8) and 3'-ACGACGGCCAGTGAATTGAA-5' (SEQ ID NO: 9) primers. Each clone was then spotted in duplicates on nylon membrane (macroarray). The dot blots were scanned with the personal fx-phospho imager (Cyclone System Packard, Meriden, CO, USA).

Protein Isolation and Western Blotting

Protein isolation and Western blotting was performed as described previously 9. Primary antibodies (Galectin-3, Bioreagents; ED-1 and OX-6, a kind gift from Dr. M. de Winther, Department of Molecular Genetics, University of Maastricht, The Netherlands) were diluted 1/1000 in tris-buffer saline with tween-20 (TBS-T). Secondary antibody (horseradish-peroxidase conjugated IgG, Cell Signaling Technology) was diluted 1/2000 in TBS-T. Protein bands were visualized by enhanced chemiluminescence (ECL, Amersham, Arlington Heights, Ill., USA) according to manufacturer's instructions.

Immunohistochemistry, Galectin Cytochemistry and Confocal Microscopy

The expression of galectin-3 and accessible binding sites were visualised by a specific anti-galectin-3 monoclonal antibody and biotinylated galectin-3, as described previously (Gabius et al., Anal Biochem.: 189: 91-94, 1990). As detailed elsewhere (Andre et al., Chembiochem. 2: 822-830, 2001) galectin-3 was biotinylated under activity-preserving conditions. In confocal laser scanning microscopy, galectin binding sites were detected by FITC-labelled avidin. A Texas-red labelled secondary antibody was used to visualise immunocytochemically the proliferating nuclear antigen (PCNA). Further details on the procedure are available elsewhere (Broers et al., J Cell Sci.: 112 (Pt 20): 3463-3475, 1999).

Cardiac Fibroblast Proliferation and Proline Incorporation Assays

Rat cardiac fibroblasts were isolated from 2-day-old neonatal Sprague-Dawley rats, as described previously (Pokharel et al., Hypertension, 40: 155-161, 2002). Cells were cultured in Dulbecco's modification of eagle's medium (DMEM) supplemented with 10% foetal bovine serum (FBS), along with 1% L-glutamate, 50 U/mL penicillin, and 0.1 g/L streptomycin, and were incubated at 37° C. in a humidified 5% $CO_2$ atmosphere. Twenty-four hours after seeding, cells were made quiescent by incubation with media containing 0.5% FBS for 24 hours. Cells were then treated with murine recombinant galectin-3 (control, 10 µg/ml and 30 µg/ml) for 24 hours. The number of dividing cells was determined by radio-labelled methyl-[$^3$H] thymidine incorporation (0.5 µCi per well) assay. Radioactivity was measured in the mixture of fibroblasts and scintillation liquid using LKB-Wallace beta counter (FSA Laboratory Supplies, Loughborough, UK).

Secreted collagen was measured using a [$^3$H]proline incorporation assay. Briefly, cardiac fibroblasts were seeded in 6-well plates at 90-100% confluency. During the final 24 hours of incubation, 15 µCi/ml of L-[$^3$H]proline was added. Incorporated [$^3$H] proline from the condition medium was precipitated with 10% trichloroacetic acid (TCA) and counted with the scintillation counter.

Statistical Analyses

Data are presented as mean±SEM. The data for each study were compared using one-way analysis of variances (ANOVA) in combination with a Dunnett post-hoc analysis to correct for multiple comparisons, using SD rats as internal control cohort. Analyses were performed using the statistical package SPSS 10.0 (Chicago, Ill., USA). P-values<0.05 were considered to be statistically significant.

Results

Deteriorated Cardiac Function and Cardiac Fibrosis in HF-S Rats

Hypertrophied left and right ventricles in 8 placebo-treated rats were observed. In contrast, there was no increase in LV in candesartan treated rats and non-transgenic controls. Four out of 8 rats without treatment developed overt clinical HF between 12-14 weeks of age, which was accompanied by indices of depressed cardiac function. The remaining 4 rats remained compensated during the study period of 17 weeks. Overt HF with pleural effusion (lung weight/body weight %: HF-S, 10.61±0.7 vs HF-R, 4.97±0.2, P<0.001) and elevated left ventricular end-diastolic pressure (LVEDP) was apparent in HF-S rats, which was not present in HF-R and or ARE treated rats (FIG. 6 a, b and c). At 10 weeks all the placebo-treated Ren-2 rats had LVH but no haemodynamic evidence for decompensation (LV weight/body weight %: Ren-2, 3.88±0.08 vs non-transgenic controls 2.15±0.2, and $dP/dt_{max}$: Ren-2, 8556±296 vs non-transgenic controls 8780±373). Myocardial collagen content, determined by computer-assisted densitometry, revealed higher degree of cardiac fibrosis in the HF-S rats compared to HF-R rats. ARB normalized LVH and myocardial collagen content so that it remained comparable to that of the normotensive background strains (FIG. 7).

Microarray Reveals Abundance of Immune-Related Genes in HF Susceptible Rats

Firstly, we examined the biological variability in gene expression between HF-S and HF-R groups. The expression levels of most genes between pairs of samples from both groups were highly correlated. We focused on the differentially expressed genes between the failing and non-failing hypertrophied hearts. Log transformation of the values was done and only statistically significant (P<0.05) differences in expression levels exceeding the 2-fold threshold were considered to be differentially expressed. Galectin-3 emerged as the most prominently overexpressed gene with more than 5-fold rise in HF rats (Table 3). Of interest, major histocompatibity complex antigen II (MHC-II) and immunoglobulin receptors genes were among these overexpressed genes.

Macroarray Reveals Normalization of HF Susceptibility Genes by Angiotensin II Blockade To validate the differentially expressed genes in HF, we first confirmed the identity of the clones by sequencing and consequently re-spotted these genes onto nylon membrane (macroarray) for repeat hybridization in separate biological samples. This also yielded an overexpression of seven major index genes initially identified by microarray. To confirm the role of renin-angiotensin system (RAS) activation in this angiotensin driven model of HF, we re-assessed the expression of the target genes identified by microarray after treating a subgroup of Ren-2 rats with a subpressor dose of candesartan from seven till 13 weeks of age. Angiotensin II blockade completely prevented the development of cardiac hypertrophy and failure. On the level of gene expression, it prevented the overexpression of all HF-related candidate genes. Notably, galectin-3 gene expression was also prevented.

Western Blotting Shows High Galectin-3 Expression in Failing Myocardium

Given the robust transcriptomal increase in galectin-3, we focused on its protein levels in the myocardium. Comparable to the results obtained in micro/macroarrays, the highest level of galectin-3 expression was observed in the same group of animals that had highest degree of cardiac fibrosis and rapidly developed cardiac decompensation by 13 weeks (HF-S, 94.6±8.9; HF-R, 35±5.6; P<0.01) (FIG. 8 a and b).

Co-Localization of CD68 Positivity, MHC-II Antigen and Galectin-3

We monitored the distribution of galectin-3 in the rat myocardium by immunohistochemistry. Histologically, HF susceptible rats revealed patchy areas of and fibrosis. The architecture of the tissues in non-affected areas was well preserved. In contrast, these areas of high fibrosis were not seen in ARE treated and SD rats, and also not in hypertrophied non-failing HF-R rats. Importantly, galectin-3 positive areas showed pronounced tissue damage and high level of fibrosis. Morphologically, galectin-3 positive cells were rather large. To confirm the assumption that these cells were macrophages, we analyzed the serial sections with a macrophage specific antibody (ED-1). Galectin-3 positive areas co-localized with the macrophage specific staining. These macrophages strongly expressed MHC-II antigen too, indicating an active role of these cells in antigen presentation. These characteristics were not evident in HF-R rats and non-transgenic controls.

Galectin-3 Binding Sites in Cardiac Fibroblasts

Having defined strong expression of galectin-3 in macrophages, we determined whether galectin-3 binds to cardiac fibroblasts. We used the biotinylated galectin-3 to visualize galectin-3 binding sites on cardiac fibroblasts. In 0.1% Triton-permeabilised cells, presence of galectin-3 binding sites resulted in diffuse cytoplasmic as well as perinuclear staining in resting cells (FIG. 10 a). In contrast, proliferating fibroblasts showed enhanced staining around the nucleus, revealing a mitosis-related alteration in staining profile (FIG. 10 b). This pattern was independently monitored by confocal microscopy. In fact, these experiments confirmed compact presence of accessible galectin-3 ligands around the nucleus in proliferating (i.e., PCNA positive) cardiac fibroblasts (FIG. 10 c, d and e) evocative of reflecting cell cycle activation in galectin-3 overexpressed state.

Galectin-3 Induced Fibroblast Proliferation and Collagen Production

Having thus provided evidence for presence of accessible sites in the cardiac fibroblasts, we determined whether galectin-3 stimulates the growth of cardiac fibroblasts. Using recombinant galectin-3, we performed proliferation assays. Galectin-3 was added in different concentrations (0, 10 and 30 μg/ml) with and without serum enrichment. We observed significant increase in cardiac fibroblast proliferation with 10 and 30 μg/ml exogenous galectin-3 over 24 hours (galectin-3 at 30 μg/ml, 347±17.5 counts per minute (cpm); galectin-3 at 10 μg/ml 309±4.8 cpm; control, 145±4.8; p<0.01). We then monitored the collagen production by cardiac fibroblasts with the addition of exogenous galectin-3 using radioactive proline-incorporation assays. With 30 μg/ml of galectin-3 in the medium, the proline incorporation increased by approximately 66% (galectin-3 at 30 μg/ml, 1066±56 cpm; control, 707±52.8 cpm; p<0.05). Lower concentration of galectin-3 failed to produce significant effects (galectin-3 at 10 μg/ml 992±72 cpm; p=0.13).

Myocardial Biopsy at 10 Weeks Showed High Galectin-3 Expression in Rats that Later Rapidly Progressed to HF To evaluate the expression status of galectin-3 in the myocardium before HF became hemodynamically and clinically apparent (i.e., 10 weeks of age) we developed a technique to obtain cardiac biopsies in the spontaneously beating rat heart. After biopsy, the rat was allowed to recover to determine whether it would prove to be resilient or rather susceptible to HF. Measured by real-time PCR, myocardial expression of galectin-3 gene was increased only in the rats that later progressed to HF (arbitrary units, 5.8±0.17), while it was expressed at relatively lower levels in the rats that subsequently remained compensated (3.4±0.2), and in non-transgenic control rat hearts (2.5±0.033) (FIG. 12).

Discussion

The current study aimed to identify the mechanisms recruited specifically in the hypertrophied ventricles transited to failure. We demonstrated that galectin-3, a macrophage expressed protein, is early and specifically expressed in failure-prone hypertrophied hearts. Furthermore, we establish that galectin-3 binds to intracellular binding sites in cardiac fibroblasts and activates cardiac fibroblast proliferation and collagen production, suggesting that this can contribute to myocardial stiffness and probably progression towards HF.

Previous studies have suggested a role for macrophages and inflammatory responses in HF. These studies, however, have left the question unanswered whether macrophage activation preceded or merely accompanied HF. Furthermore, an explanation on the specific mechanisms that link macrophages to cardiac fibrosis was also lacking.

Identified first as an antigen on the surface of peritoneal macrophages, galectin-3 is the only chimera-type member of the galectin family. It has a lectin group sharing calcium-independent specificity to β-galactosides as well as proteins and is located in the phagocytic cups and phagosomes of the macrophages. Besides its anti-apoptotic and growth promoting actions, galectin-3 also regulates monocyte chemotaxis, chemokinesis and modulates the availability of cytokines. Furthermore, recent studies have also suggested that galectin-3 plays a critical role in phagocytosis by macrophages when cross-linked by Fcγ receptor (FcγR).

Interestingly, we also observed the overexpression of FcγR in our HF models (Table 3).

The biopsy obtained from 10-week old rats showed an increased galectin-3 expression only in the rats that transited to rapid failure. Given the pro-inflammatory and fibroblast growth promoting actions of galectin-3, the increased expression at this stage may contribute to a failure-conducive environment. In accordance with our findings, galectin-3 expressed by liver-analogues of macrophages (i.e., kupffer cells), have been implicated to induce the synthesis of excess fibril-forming collagens in liver. This suggests that galectin-3 is a macrophage related pro-fibrotic mediator and yet another inflammatory infiltrate cytokine with the potential to influence cardiac remodeling in conditions characterized by macrophage infiltration. An alternative hypothesis on how galectin-3 could add to the progression towards HF emerges from the discovery of galectin-3 as the third receptor for advanced glycosylation end-products (RAGE-3), that have critical role in collagen cross-linking and myocardial stiffness.

We also document that galectin-3 binds to intracellular receptors and induces cardiac fibroblast proliferation and accentuates collagen production. Though originally discovered as a carbohydrate binding protein, galectin-3 is known to specifically interact with intracellular targets besides glycoconjugates. Previous studies have proposed several molecules as galectin-3 binding sites including, Mac-2 binding protein, and laminin. However, it is still not known what induces the rapid perinuclear migration of galectin-3 binding elements in proliferating cells. Whether it is an export of galectin-3 binding sites from the dividing nucleus (centrifugal migration) or it is a directed cytosolic to nuclear transition (centripetal migration) of these receptors, needs further exploration.

The current study suggests a key role for immune system activation and galectin-3 production in the progression from left ventricular hypertrophy to HF and demonstrates a link between pro-immune and pro-fibrotic factors. The increased expression of galectin-3 preceding HF can reflect the early and aberrant activation of macrophages in hypertrophied failing ventricles. Galectin-3, in turn, can relay signals from activated macrophages to cardiac fibroblasts. Peripheral detection of galectin-3 can serve as a predictor of HF and therapeutic inhibition of galectin-3 action can become a novel therapeutic target to counteract excess cardiac fibrosis.

Example 3

Evaluation of Galectin-3 in Human Serum

Galectin-3 levels were measured in the serum of patients with cardiovascular disease. A commercially available kit to measure galectin-3 by ELISA was employed. The results are summarized in Table 4-6. It was shown that Galectin-3 is significantly elevated in the serum of patients with cardiovascular disease such as heart failure, LVH. Moreover, an upper limit for galectin-3 levels in healthy control subjects was found, which is surpassed in most CHF patients.

According to the present invention it has thus for the first time been demonstrated that measurement of galectin-3 in the serum of human subjects reliably distinguishes diseased from non-diseased subjects, and thus provides additional information on non-myocytic disease processes, in conjunction with known myocytic markers (BNP).

Data Tables:

LVH=hypertensives, hypertrophy

CHF=heart failure

Infl=inflammatory vascular disease

Poscon=mixed group of diseases

Infarct=infarction patients

Healthy=healthy controls

TABLE 1

Sequences of real-time quantitative RT-PCR primers and probes of candidate gene transcripts

| Gene/primer | Sequence (5'→3') | Position | Species |
|---|---|---|---|
| Cyclophilin A (M19533) | | | |
| Fwd | GGGAGAAAGGAT TTGGCTATAAGG (SEQ ID NO: 10) | 167-190 | Rat |
| Probe | TGAAGTCACCACC CTGGCACATGAAT (SEQ ID NO: 11) | 219-244 | |
| Rev | GCCACCAGTGCCATTATGG (SEQ ID NO: 12) | 249-267 | |
| Thrombospondin 2 (XM_214778) | | | |
| Fwd | GAAATGGTCTACTT CTCAGACCTCAAG (SEQ ID NO: 13) | 603-629 | Rat |
| Probe | CCCTGCTCTCTAGGC ATCTCTGCACTCAT (SEQ ID NO: 14) | 631-659 | |

TABLE 1-continued

Sequences of real-time quantitative RT-PCR primers and probes of candidate gene transcripts

| Gene/primer | Sequence (5'→3') | Position | Species |
|---|---|---|---|
| Rev | GCACACTGCTGGAGCTGGA (SEQ ID NO: 15) | 791-809 | |
| Osteoactivin (NM_002510) | | | |
| Fwd | GGACTTCATTGTGACCTGCAAA (SEQ ID NO: 16) | 1350-1371 | Rat |
| Probe | CCACTCCCACGGAAGCCTGTACGAT (SEQ ID NO: 17) | 1376-1400 | |
| Rev | ACCCTGTTCTGGGCGATCT (SEQ ID NO: 18) | 1421-1439 | |
| Collagen VI (TC322135) | | | |
| Fwd | CCCTCCTTGCAGGCAGAAC (SEQ ID NO: 19) | 816-834 | Rat |
| Probe | ATGCCTTGCAGATCAATAACACAGCAGTAGG (SEQ ID NO: 20) | 845-875 | |
| Rev | CAGGAGGACCGAGAGCTCAT (SEQ ID NO: 21) | 897-916 | |
| Brain natriuretic peptide (M25297) | | | |
| Fwd | GCTGCTTTGGGCAGAAGATAGA (SEQ ID NO: 22) | 350-371 | Rat |
| Probe | CCTCAGCCCGTCACAGCCCAA (SEQ ID NO: 23) | 394-414 | |
| Rev | GCCAGGAGGTCTTCCTAAAACA (SEQ ID NO: 24) | 416-437 | |

The probes were labelled at the 5' and 3' positions with 6-carboxyfluorescein reporter and 6-carboxytetramethylrhodamine quencher, respectively. The position of the primers and probes were annotated according to the sequences derived from GenBank (accession numbers given in parenthesis). Fwd, forward; Rev, reverse.

TABLE 3

Sequences for semi-quantitative PCR and real-time quantitative RT-PCR primers and probes of candidate gene transcripts

| Gene/primer | Sequence (5'→3') | Species |
|---|---|---|
| Cyclophilin A (NM_021130) | | |
| Fwd | TGCTGGACCCAACACAAATG (SEQ ID NO: 25) | Human |
| Probe | TTCCCAGTTTTTCATCTGCACTGCCA (SEQ ID NO: 26) | |
| Rev | TGCCATCCAACCACTCAGTC (SEQ ID NO: 27) | |
| Galectin-3 (NM_002306) | | |
| Fwd | CTCGCATGCTGATAACAATTCTG (SEQ ID NO: 28) | Human |
| Probe | CGGTGAAGCCCAATGCAAACAGAATT (SEQ ID NO: 29) | |
| Rev | GCAACATCATTCCCTCTTTGG (SEQ ID NO: 30) | |
| MCP-1 (M57441) | | |
| Fwd | GCAGGTCTCTGTCACGCTTCT (SEQ ID NO: 31) | Rat |
| Rev | GATGATCCCAATGAGTCGGCT (SEQ ID NO: 32) | |

The probes were labelled at the 5' and 3' positions with 6-carboxyfluorescein reporter and 6-carboxytetramethylrhodamine quencher, respectively. The position of the primers and probes were annotated according to the sequences derived from GenBank (accession numbers given in parenthesis). Fwd, forward; Rev, reverse.

TABLE 2

Comparison of hemodynamic parameters at 10-week (hypertrophy, no HF), 12 to 14-week (progressed to established HP) and 17-week (compensated hypertrophy) rats

| | 10 weeks (n = 8) | | 12-14 weeks (n = 6) | | 17 weeks (n = 8) | |
|---|---|---|---|---|---|---|
| Parameters | SD | Ren-2 | SD | Ren-2 | SD | Ren-2 |
| LVW/BW | 2.15 ± 0.2 | 3.88 ± 0.08* | 2.21 ± 0.5 | 3.91 ± 0.9* | 2.57 ± 0.12 | 3.60 ± 0.5* |
| $dP/dt_{max}$ | 9010 ± 373 | 8556 ± 296 | 9297 ± 221 | 3764 ± 198*,# | 7612 ± 124 | 7814 ± 658 |
| $-dP/dt_{max}$ | 8943 ± 976 | 8200 ± 482 | 9648 ± 514 | 3251 ± 312*,# | 6937 ± 845 | 6967 ± 654 |

LVW/BW, left ventricular weight corrected for body weight; $dP/dt_{max}$ (mmHg/s), maximum rate of LV pressure rise; $-dP/dt_{min}$, maximum rate of LV pressure fall;
*$P < 0.05$ vs age matched SD rats;
$P < 0.01$ vs 10-week and 17-week Ren-2 rats.

TABLE 4

Galectin-3, descriptives

|  | N | Mean | Std. Deviation | Std. Error | 95% Confidence Interval for Mean | | Minimum | Maximum |
|---|---|---|---|---|---|---|---|---|
|  |  |  |  |  | Lower Bound | Upper Bound |  |  |
| LVH | 22 | 6.253 | 1.457 | .311 | 5.607 | 6.899 | 3.7 | 8.8 |
| chf | 39 | 9.392 | 1.845 | .295 | 8.794 | 9.990 | 5.0 | 13.1 |
| infl | 15 | 7.427 | 1.678 | .433 | 6.498 | 8.356 | 4.6 | 10.5 |
| poscon | 3 | 6.660 | .871 | .503 | 4.496 | 8.824 | 5.9 | 7.6 |
| infarct | 6 | 6.317 | 1.262 | .515 | 4.992 | 7.641 | 5.3 | 8.5 |
| healthy | 26 | 4.717 | 1.125 | .221 | 4.262 | 5.171 | 2.8 | 6.8 |
| Total | 111 | 7.169 | 2.390 | .227 | 6.720 | 7.619 | 2.8 | 13.1 |

TABLE 5

ANOVA

|  | Sum of Squares | df | Mean Square | F | Sig. |
|---|---|---|---|---|---|
| Between Groups | 373.605 | 5 | 74.721 | 30.832 | .000 |
| Within Groups | 254.464 | 105 | 2.423 |  |  |
| Total | 628.069 | 110 |  |  |  |

TABLE 6

Multiple comparisons. Dependent variable: Galectin-3 Bonferroni

| (I) GROUP | (J) GROUP | Mean Difference (I − J) | Std. Error | Sig. | 95% Confidence Interval | |
|---|---|---|---|---|---|---|
|  |  |  |  |  | Lower Bound | Upper Bound |
| LVH | chf | −3.139* | .415 | .000 | −4.385 | −1.892 |
|  | infl | −1.173 | .521 | .397 | −2.739 | .392 |
|  | poscon | −.407 | .958 | 1.000 | −3.285 | 2.471 |
|  | infarct | −6.348E−02 | .717 | 1.000 | −2.217 | 2.090 |
|  | healthy | 1.536* | .451 | .014 | .182 | 2.891 |
| chf | LVH | 3.139* | .415 | .000 | 1.892 | 4.385 |
|  | infl | 1.965* | .473 | .001 | .544 | 3.386 |
|  | poscon | 2.732 | .933 | .063 | −6.994E−02 | 5.534 |
|  | infarct | 3.075* | .683 | .000 | 1.024 | 5.126 |
|  | healthy | 4.675* | .394 | .000 | 3.491 | 5.859 |
| infl | LVH | 1.173 | .521 | .397 | −.392 | 2.739 |
|  | chf | −1.965* | .473 | .001 | −3.386 | −.544 |
|  | poscon | .767 | .985 | 1.000 | −2.191 | 3.724 |
|  | infarct | 1.110 | .752 | 1.000 | −1.149 | 3.369 |
|  | healthy | 2.710* | .505 | .000 | 1.194 | 4.226 |
| poscon | LVH | .407 | .958 | 1.000 | −2.471 | 3.285 |
|  | chf | −2.732 | .933 | .063 | −5.534 | 6.994E−02 |
|  | infl | −.767 | .985 | 1.000 | −3.724 | 2.191 |
|  | infarct | .343 | 1.101 | 1.000 | −2.963 | 3.650 |
|  | healthy | 1.943 | .949 | .647 | −.908 | 4.794 |
| infarct | LVH | 6.348E−02 | .717 | 1.000 | −2.090 | 2.217 |
|  | chf | −3.075* | .683 | .000 | −5.126 | −1.024 |
|  | infl | −1.110 | .752 | 1.000 | −3.369 | 1.149 |
|  | poscon | −.343 | 1.101 | 1.000 | −3.650 | 2.963 |
|  | healthy | 1.600 | .705 | .380 | −.518 | 3.718 |
| healthy | LVH | −1.536* | .451 | .014 | −2.891 | −.182 |
|  | chf | −4.675* | .394 | .000 | −5.859 | −3.491 |
|  | infl | −2.710* | .505 | .000 | −4.226 | −1.194 |
|  | poscon | −1.943 | .949 | .647 | −4.794 | .908 |
|  | infarct | −1.600 | .705 | .380 | −3.718 | .518 |

*The mean difference is significant at the .05 level.

The invention claimed is:

1. A method for identifying a subject at risk of progression of heart failure, the method comprising measuring the level of galectin-3 in a biological sample from a human subject and comparing the level of galectin-3 to a standard level indicative of risk of progression of heart failure, wherein an elevated level of galectin-3 in the sample indicates a risk of progression of heart failure.

2. The method of claim 1, wherein the sample is a serum or plasma sample derived from peripheral blood.

3. The method of claim 1, wherein the standard level is a level indicative of the risk of progression of congestive heart failure.

4. The method of claim 1, wherein the standard level is based on the level of galectin-3 in healthy subjects.

5. The method of claim 1, wherein the biological sample is from a patient with cardiovascular disease.

6. The method of claim 1, further comprising measuring the level of thrombospondin-2 in the sample and comparing the level of thrombospondin-2 to a standard level indicative of risk of progression of heart failure.

* * * * *

SEQUENCE LISTING

<160> NUMBER OF SEQ ID NOS: 32

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggtgacacta tagaagagc                                                    19

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
accatgatta cgccaagctc                                                   20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
acgacggcca gtgaattgaa                                                   20

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cccgactgga ccactgaca                                                    19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cagcatgcga ggcatgact                                                    19

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
tgccctacga tatgcccttg cctg                                              24

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggtgacacta tagaagagc                                                    19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
accatgatta cgccaagctc                                                   20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acgacggcca gtgaattgaa                                                   20

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gggagaaagg atttggctat aagg                                              24

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
tgaagtcacc accctggcac atgaat                                            26

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gccaccagtg ccattatgg                                                    19

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gaaatggtct acttctcaga cctcaag                                        27

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
ccctgctctc taggcatctc tgcactcat                                      29

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcacactgct ggagctgga                                                 19

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggacttcatt gtgacctgca aa                                             22

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
ccactcccac ggaagcctgt acgat                                          25

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
accctgttct gggcgatct                                                 19

<210> SEQ ID NO 19

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ccctccttgc aggcagaac                                                    19

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
atgccttgca gatcaataac acagcagtag g                                      31

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
caggaggacc gagagctcat                                                   20

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gctgctttgg gcagaagata ga                                                22

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
cctcagcccg tcacagccca a                                                 21

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gccaggaggt cttcctaaaa ca                                                22

<210> SEQ ID NO 25
<211> LENGTH: 20
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 25
tgctggaccc aacacaaatg                                                    20

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
ttcccagttt ttcatctgca ctgcca                                             26

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tgccatccaa ccactcagtc                                                    20

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ctcgcatgct gataacaatt ctg                                                23

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
cggtgaagcc caatgcaaac agaatt                                             26

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gcaacatcat tccctctttg g                                                  21

<210> SEQ ID NO 31
<211> LENGTH: 21
<212> TYPE: DNA
<213> ORGANISM: Artificial Sequence
<220> FEATURE:

-continued

```
<223> OTHER INFORMATION: Description of Artificial Sequence: Synthetic
      primer

<400> SEQUENCE: 31
gcaggtctct gtcacgcttc t                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gatgatccca atgagtcggc t                                              21
```